(12) United States Patent
de Juan, Jr. et al.

(10) Patent No.: US 8,691,265 B2
(45) Date of Patent: *Apr. 8, 2014

(54) DRUG DELIVERY METHODS, STRUCTURES, AND COMPOSITIONS FOR NASOLACRIMAL SYSTEM

(71) Applicant: Mati Therapeutics, Inc., Austin, TX (US)

(72) Inventors: Eugene de Juan, Jr., San Francisco, CA (US); Stephen Boyd, Murrieta, CA (US); Hanson S. Gifford, III, Woodside, CA (US); Mark Deem, Mountain View, CA (US); Cary J. Reich, Los Gatos, CA (US)

(73) Assignee: Mati Therapeutics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/645,261

(22) Filed: Oct. 4, 2012

(65) Prior Publication Data

US 2013/0101658 A1 Apr. 25, 2013

Related U.S. Application Data

(63) Continuation of application No. 12/332,219, filed on Dec. 10, 2008, now abandoned, which is a continuation of application No. 11/695,537, filed on Apr. 2, 2007.

(60) Provisional application No. 60/871,864, filed on Dec. 26, 2006, provisional application No. 60/787,775, filed on Mar. 31, 2006.

(51) Int. Cl.
*A61F 13/00* (2006.01)
*A61F 2/00* (2006.01)

(52) U.S. Cl.
USPC ............................. 424/427; 424/422; 424/423

(58) Field of Classification Search
None
See application file for complete search history.

(56) References Cited

U.S. PATENT DOCUMENTS 3,865,108 A 2/1975 Hartop
3,949,750 A 4/1976 Freeman
(Continued)

FOREIGN PATENT DOCUMENTS

EP 0442745 A1 8/1991
EP 0621022 A1 10/1994
(Continued)

OTHER PUBLICATIONS

Notification of the Second Office Action as issued for Chinese Patent Application No. 200780017166.2, dated Mar. 6, 2012.

(Continued)

*Primary Examiner* — Carlos Azpuru
*Assistant Examiner* — Casey Hagopian
(74) *Attorney, Agent, or Firm* — Koren Anderson; Mati Therapeutics Inc.

(57) ABSTRACT

A drug insert is configured for use with an implant. The implant is configured for insertion into a lacrimal canaliculus. The drug insert includes a drug core comprising a therapeutic agent and a polymer; and a sheath body comprising material substantially impermeable to the therapeutic agent, wherein the drug core is positioned within the sheath body. The sheath body is configured to provide an exposed end of the drug core that releases therapeutic agent to an eye when the drug insert is disposed within the implant and the implant is positioned in the lacrimal canaliculus. A distal end of the drug core is sealed with a medical-grade adhesive.

17 Claims, 25 Drawing Sheets

(56) References Cited

U.S. PATENT DOCUMENTS

| | | |
|---|---|---|
| 4,014,335 A | 3/1977 | Arnold |
| 4,281,654 A | 8/1981 | Shell et al. |
| 4,660,546 A | 4/1987 | Herrick et al. |
| 4,886,488 A | 12/1989 | White |
| 4,915,684 A | 4/1990 | MacKeen et al. |
| 4,959,048 A | 9/1990 | Seder et al. |
| 5,041,081 A | 8/1991 | Odrich |
| 5,049,142 A | 9/1991 | Herrick et al. |
| 5,053,030 A | 10/1991 | Herrick et al. |
| 5,128,058 A | 7/1992 | Ishii et al. |
| 5,133,159 A | 7/1992 | Nelson |
| 5,163,959 A | 11/1992 | Herrick |
| 5,171,270 A | 12/1992 | Herrick |
| 5,254,089 A | 10/1993 | Wang |
| 5,283,063 A | 2/1994 | Freeman |
| 5,318,513 A | 6/1994 | Leib |
| 5,334,137 A | 8/1994 | Freeman |
| 5,395,618 A | 3/1995 | Darougar et al. |
| 5,417,651 A | 5/1995 | Guena et al. |
| 5,423,777 A | 6/1995 | Tajiri et al. |
| 5,466,233 A | 11/1995 | Weiner et al. |
| 5,556,633 A | 9/1996 | Haddad et al. |
| 5,707,643 A | 1/1998 | Ogura et al. |
| 5,723,005 A | 3/1998 | Herrick |
| 5,766,243 A | 6/1998 | Christensen et al. |
| 5,773,019 A | 6/1998 | Ashton et al. |
| 5,824,073 A | 10/1998 | Peyman |
| 5,826,584 A | 10/1998 | Schmitt |
| 5,830,171 A | 11/1998 | Wallace |
| 5,840,054 A | 11/1998 | Hamano et al. |
| 5,902,598 A | 5/1999 | Chen et al. |
| 5,928,662 A | 7/1999 | Phillips |
| 5,961,370 A | 10/1999 | Valle et al. |
| 5,962,383 A | 10/1999 | Doyel et al. |
| 5,993,407 A | 11/1999 | Moazed |
| 6,010,391 A | 1/2000 | Lewellen et al. |
| 6,016,806 A | 1/2000 | Webb |
| 6,027,470 A | 2/2000 | Mendius |
| 6,041,785 A | 3/2000 | Webb |
| 6,082,362 A | 7/2000 | Webb |
| 6,095,901 A | 8/2000 | Robinson et al. |
| 6,149,684 A | 11/2000 | Herrick |
| 6,196,993 B1 | 3/2001 | Cohan et al. |
| 6,225,348 B1 | 5/2001 | Paulsen |
| 6,234,175 B1 | 5/2001 | Zhou et al. |
| 6,238,363 B1 | 5/2001 | Kurihashi |
| 6,254,562 B1 | 7/2001 | Fouere |
| 6,264,971 B1 | 7/2001 | Darougar et al. |
| 6,290,684 B1 | 9/2001 | Herrick |
| 6,306,114 B1 | 10/2001 | Freeman et al. |
| 6,331,313 B1 | 12/2001 | Wong et al. |
| 6,371,122 B1 | 4/2002 | Mandelkorn |
| 6,375,972 B1 | 4/2002 | Guo et al. |
| 6,383,192 B1 | 5/2002 | Kurihashi |
| 6,416,780 B1 | 7/2002 | Passmore et al. |
| 6,428,502 B1 | 8/2002 | Lang |
| 6,455,062 B1 | 9/2002 | Olejnik et al. |
| 6,605,108 B2 | 8/2003 | Mendius et al. |
| 6,629,533 B1 | 10/2003 | Webb et al. |
| 6,645,963 B2 | 11/2003 | Higashiyama et al. |
| 6,706,275 B1 | 3/2004 | Camp |
| 6,729,939 B2 | 5/2004 | Wrue |
| 6,756,049 B2 | 6/2004 | Brubaker et al. |
| 6,780,164 B2 | 8/2004 | Bergheim et al. |
| 6,840,931 B2 | 1/2005 | Peterson et al. |
| 6,846,318 B2 | 1/2005 | Camp |
| 6,866,563 B2 | 3/2005 | Green |
| 6,964,781 B2 | 11/2005 | Brubaker |
| 6,982,090 B2 | 1/2006 | Gillespie |
| 6,991,808 B2 | 1/2006 | Brubaker et al. |
| 6,994,684 B2 | 2/2006 | Murray et al. |
| 7,017,580 B2 | 3/2006 | Prescott et al. |
| 7,117,870 B2 | 10/2006 | Prescott |
| 7,135,009 B2 | 11/2006 | Tu et al. |
| 7,204,253 B2 | 4/2007 | Mendius et al. |
| 7,204,995 B2 | 4/2007 | El-Sherif et al. |
| 7,998,497 B2 * | 8/2011 | de Juan et al. ............... 424/423 |
| 2002/0032400 A1 | 3/2002 | Moazed |
| 2002/0055701 A1 | 5/2002 | Fischell et al. |
| 2002/0198453 A1 | 12/2002 | Herrick, II |
| 2003/0130612 A1 | 7/2003 | Moazed |
| 2004/0102729 A1 | 5/2004 | Haffner et al. |
| 2004/0116524 A1* | 6/2004 | Cohen et al. .................. 514/559 |
| 2004/0121014 A1 | 6/2004 | Guo et al. |
| 2004/0127843 A1 | 7/2004 | Tu et al. |
| 2004/0141151 A1 | 7/2004 | Gillespie |
| 2004/0144392 A1 | 7/2004 | Mueller, Jr. |
| 2004/0147870 A1 | 7/2004 | Burns et al. |
| 2004/0170685 A1 | 9/2004 | Carpenter et al. |
| 2004/0175410 A1 | 9/2004 | Ashton et al. |
| 2004/0176341 A1* | 9/2004 | Chou et al. .................... 514/179 |
| 2004/0208910 A1* | 10/2004 | Ashton et al. ................ 424/427 |
| 2004/0249333 A1 | 12/2004 | Bergheim et al. |
| 2004/0265356 A1 | 12/2004 | Mosack |
| 2005/0048121 A1 | 3/2005 | East et al. |
| 2005/0095269 A1 | 5/2005 | Ainpour et al. |
| 2005/0129731 A1 | 6/2005 | Horres et al. |
| 2005/0197614 A1 | 9/2005 | Pritchard et al. |
| 2005/0220882 A1 | 10/2005 | Pritchard et al. |
| 2005/0232972 A1* | 10/2005 | Odrich ........................... 424/427 |
| 2005/0244469 A1 | 11/2005 | Whitcup et al. |
| 2005/0244506 A1 | 11/2005 | Burke et al. |
| 2005/0266047 A1 | 12/2005 | Tu et al. |
| 2005/0271704 A1 | 12/2005 | Tu et al. |
| 2005/0283109 A1 | 12/2005 | Peyman |
| 2006/0013835 A1 | 1/2006 | Anderson et al. |
| 2006/0020248 A1 | 1/2006 | Prescott |
| 2006/0020253 A1 | 1/2006 | Prescott |
| 2006/0074370 A1 | 4/2006 | Zhou |
| 2006/0106352 A1 | 5/2006 | Kurihashi |
| 2006/0122553 A1 | 6/2006 | Hanna |
| 2007/0083146 A1 | 4/2007 | Murray |
| 2007/0123924 A1 | 5/2007 | Becker |
| 2007/0132125 A1 | 6/2007 | Rastogi et al. |
| 2007/0135914 A1 | 6/2007 | Herrick, II |
| 2007/0243230 A1 | 10/2007 | de Juan, Jr. et al. |
| 2007/0269487 A1 | 11/2007 | de Juan, Jr. et al. |
| 2007/0298075 A1 | 12/2007 | Borgia et al. |
| 2007/0299515 A1 | 12/2007 | Herrick, II |
| 2007/0299516 A1 | 12/2007 | Cui |
| 2008/0038317 A1 | 2/2008 | Chang et al. |
| 2008/0045878 A1 | 2/2008 | Bergheim et al. |
| 2008/0045911 A1 | 2/2008 | Borgia et al. |
| 2009/0092654 A1 | 4/2009 | de Juan, Jr. et al. |

FOREIGN PATENT DOCUMENTS

| | | |
|---|---|---|
| JP | 7-178130 | 7/1995 |
| JP | 10-033584 | 2/1998 |
| JP | 11-505159 | 5/1999 |
| JP | 2004-202276 | 7/2004 |
| JP | 2005-000628 | 1/2005 |
| JP | 2005-058622 | 3/2005 |
| JP | 2005-110765 | 4/2005 |
| JP | 2005-110930 | 4/2005 |
| JP | 2005-312835 | 11/2005 |
| JP | 2005-319190 | 11/2005 |
| JP | 2005-328922 | 12/2005 |
| JP | 2007-195819 | 8/2007 |
| NZ | 581461 | 4/2011 |
| WO | WO-93/12765 | 7/1993 |
| WO | WO-95/01764 | 1/1995 |
| WO | WO-95/28984 | 11/1995 |
| WO | WO-97/11655 | 4/1997 |
| WO | WO-98/33461 A1 | 8/1998 |
| WO | WO-98/42282 A1 | 10/1998 |
| WO | WO-99/37260 A1 | 7/1999 |
| WO | WO-99/44553 A1 | 9/1999 |
| WO | WO-99/64089 A1 | 12/1999 |
| WO | WO-99/65544 A1 | 12/1999 |
| WO | WO-00/27321 A1 | 5/2000 |
| WO | WO-00/62760 A1 | 10/2000 |
| WO | WO-01/80825 | 11/2001 |
| WO | WO-02/11783 A1 | 2/2002 |

(56) References Cited

FOREIGN PATENT DOCUMENTS

| | | |
|---|---|---|
| WO | WO-02/083198 A2 | 10/2002 |
| WO | WO-03/017897 A2 | 3/2003 |
| WO | WO-03/057101 A1 | 7/2003 |
| WO | WO-2004/004614 A2 | 1/2004 |
| WO | WO-2004/024043 A2 | 3/2004 |
| WO | WO-2004/105658 A1 | 12/2004 |
| WO | WO-2004/112639 A2 | 12/2004 |
| WO | WO-2005/000154 A2 | 1/2005 |
| WO | WO-2005/086694 A2 | 9/2005 |
| WO | WO-2006/014434 A2 | 2/2006 |
| WO | WO-2006/014793 A1 | 2/2006 |
| WO | WO-2006/031658 A2 | 3/2006 |
| WO | WO-2006/044669 A2 | 4/2006 |
| WO | WO-2006/096586 A1 | 9/2006 |
| WO | WO-2007/008262 A2 | 1/2007 |
| WO | WO-2007/115259 A2 | 10/2007 |
| WO | WO-2007/115261 A2 | 10/2007 |
| WO | WO-2007/149771 A2 | 12/2007 |
| WO | WO-2007/149832 A2 | 12/2007 |

OTHER PUBLICATIONS

Decision of Rejection as issued for Japanese Patent Application No. 2009-503335, dated Apr. 3, 2012.
Examination Report as issued for New Zealand Patent Application No. 571758, dated Nov. 14, 2011.
Notice of Rejection as issued for Japanese Patent Application No. 2009-503334, dated Aug. 30, 2011.
Notice of Defects issued for Israeli Patent Appln. No. 194514, dated Sep. 12, 2011.
Notice of Defects issued for Israeli Patent Appln. No. 212114, dated Sep. 12, 2011.
Office Action as issued for Korean Patent Application No. 10-2008-7026781, dated Aug. 26, 2010.
Office Action as issued for Korean Patent Application No. 10-2008-7026758, dated Oct. 25, 2010.
Office Action as issued for Canadian Patent Application No. 2,648,066, dated Nov. 1, 2010.
Examination Report as issued for New Zealand Patent Application No. 571758, dated May 24, 2010.
U.S. Appl. No. 11/695,537, Restriction Requirement mailed Oct. 3, 2008, 10 pgs.
U.S. Appl. No. 11/695,537, Response filed Nov. 3, 2008 to Restriction Requirement mailed Oct. 3, 2008, 15 pgs.
U.S. Appl. No. 11/695,545, Preliminary Amendment and Response filed Nov. 6, 2008 to Restriction Requirement mailed Oct. 6, 2008, 14 pgs.
U.S. Appl. No. 11/695,545, Restriction Requirement mailed Oct. 6, 2008, 10 pgs.
International Application Serial No. PCT/US07/65792, International Search Report mailed on Nov. 20, 2008, 2 pgs.
International Application Serial No. PCT/US07/65792, International Written Opinion mailed on Nov. 20, 2008, 5 pgs.
International Application Serial No. PCT/US2007/065789, International Search Report mailed on Aug. 13, 2008, 3 pgs.
International Application Serial No. PCT/US2007/065789, International Written Opinion mailed on Aug. 13, 2008, 5 pgs.
Crisp, Abstract for Grant No. 1R43EY012916-01, "Time Release Ophthalmic Drug Delivery Insert", published on or about Jan. 21, 2000; http://crisp.cit.nih.gov/crisp/CRISP_LIB.getdoc?textkey+6073940&p_grant_num=1R43EY012916-01&p_query=&ticket=63935662&p_audit_session_id=320568793&p_keywords=.

* cited by examiner

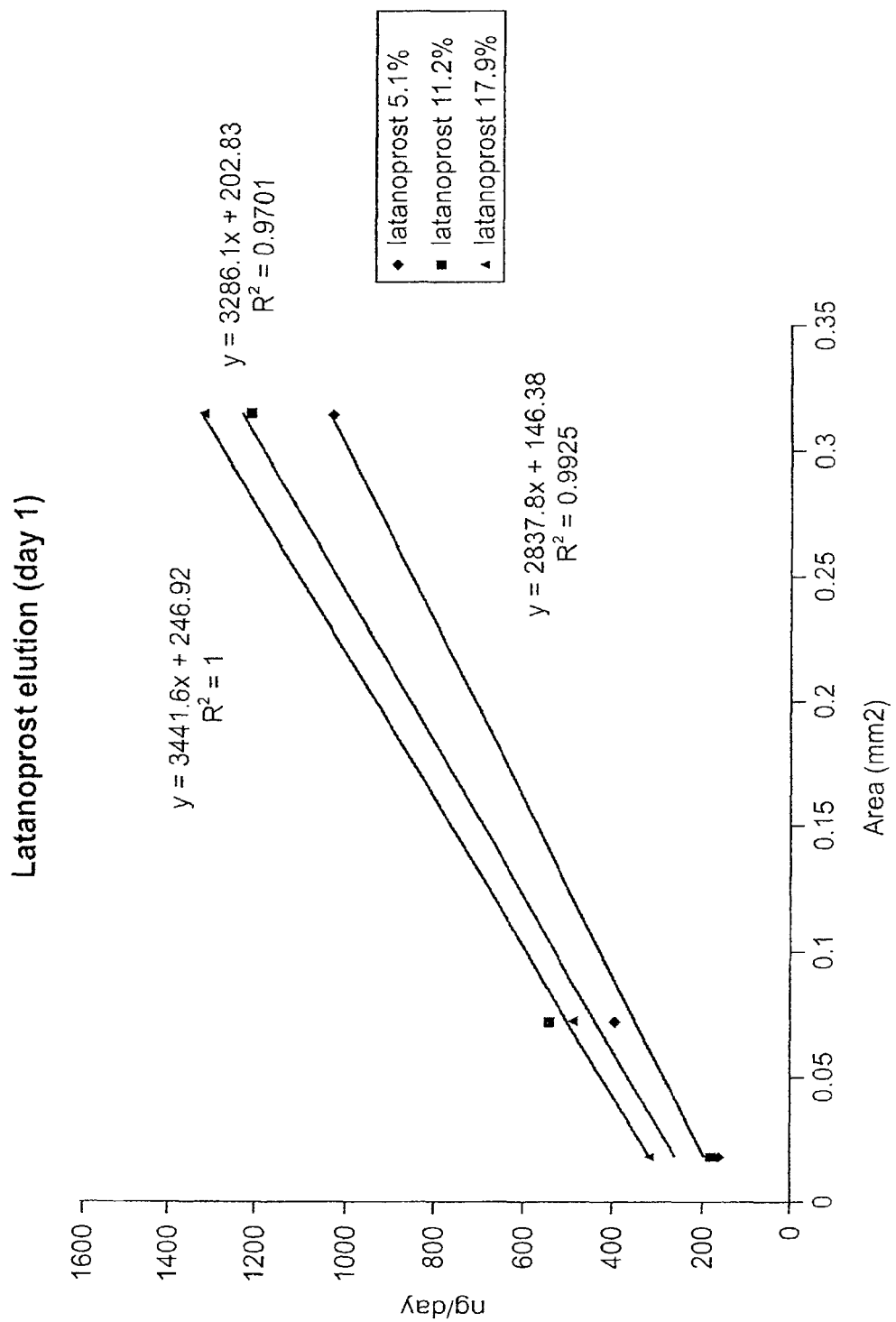

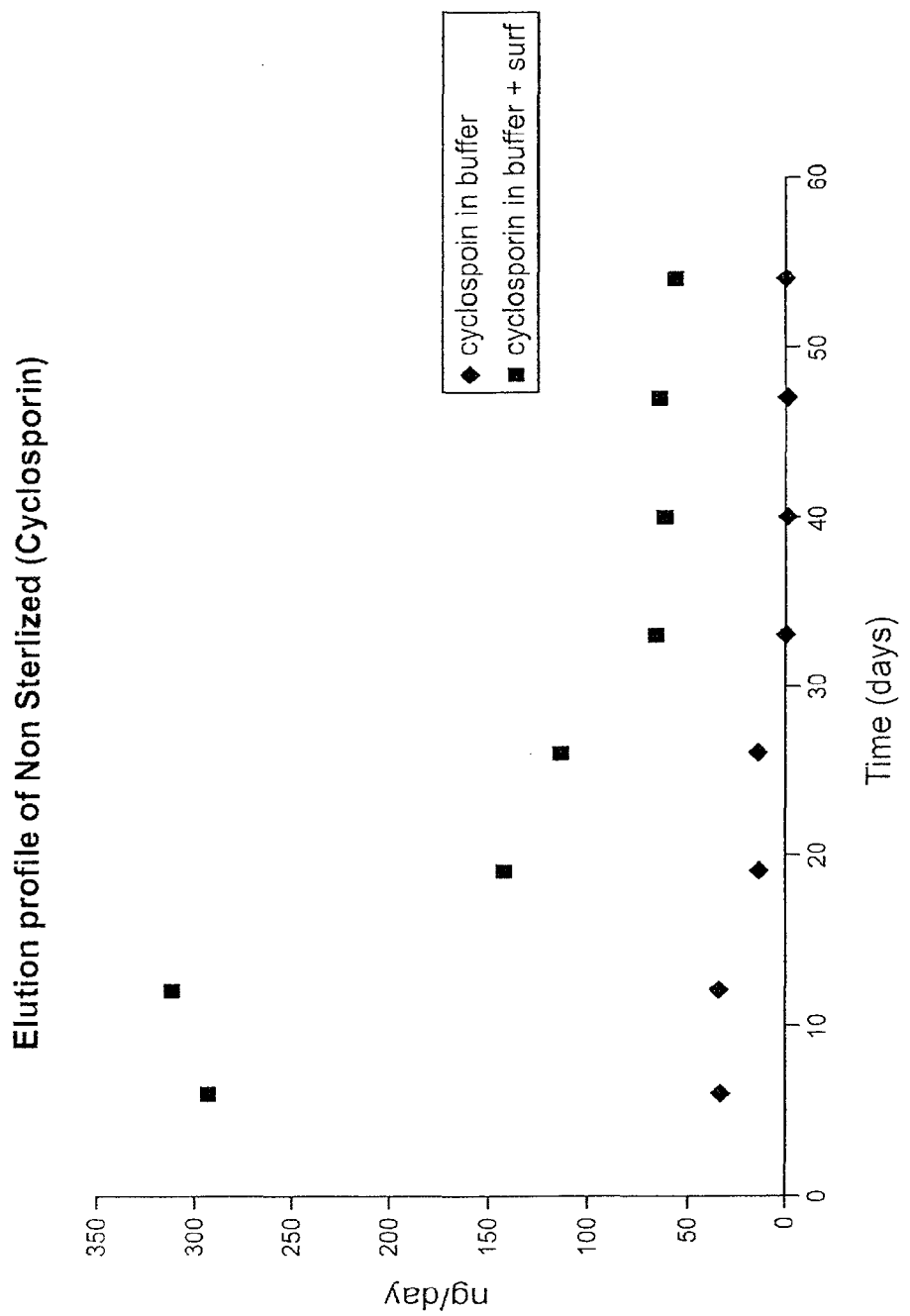

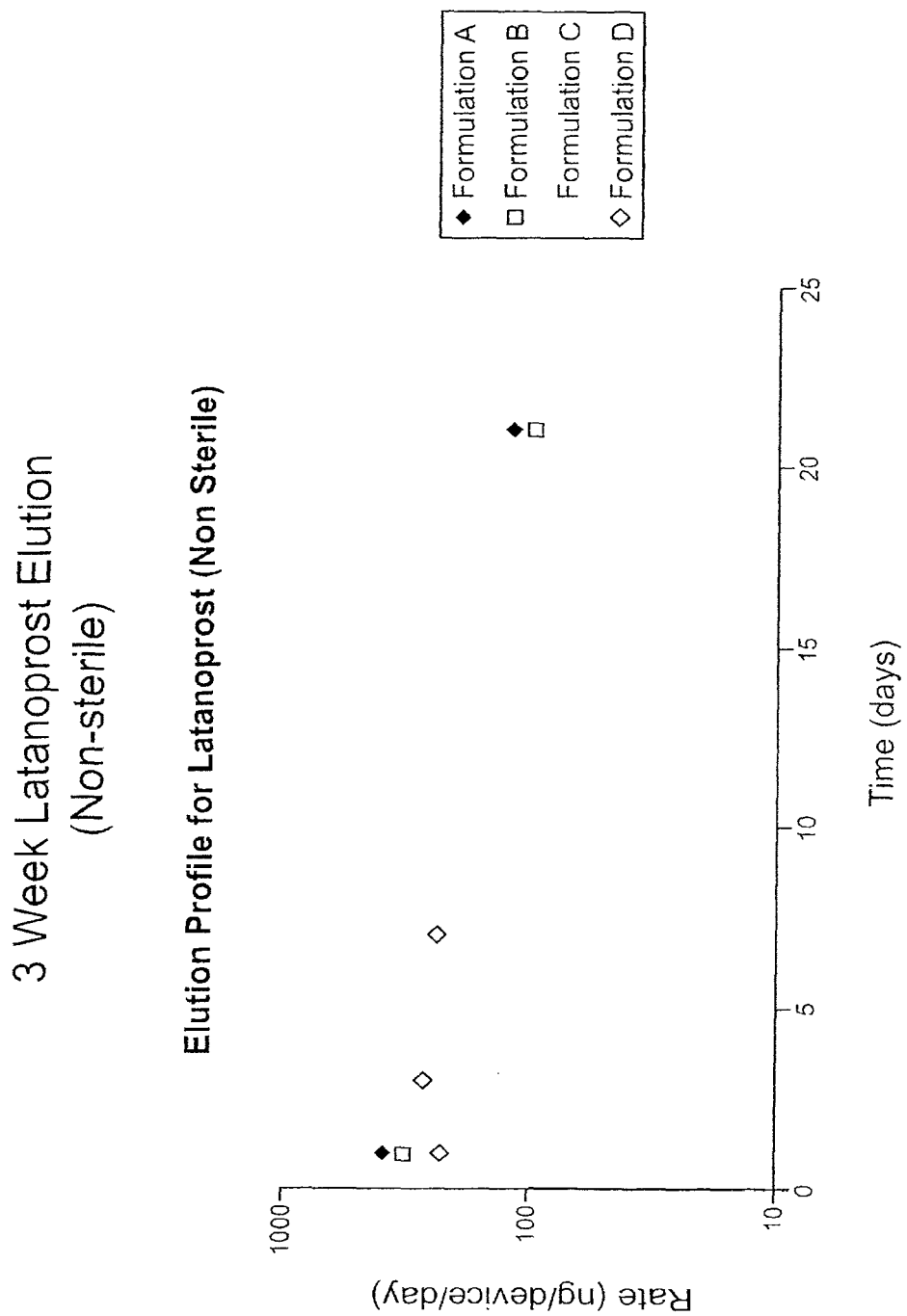

DRUG DELIVERY METHODS, STRUCTURES, AND COMPOSITIONS FOR NASOLACRIMAL SYSTEM

CROSS-REFERENCES TO RELATED APPLICATIONS

This application is a continuation application of U.S. patent application Ser. No. 12/332,219, filed Dec. 10, 2008 and currently pending, which is a continuation of U.S. patent application Ser. No. 11/695,537, filed Apr. 2, 2007 and currently pending, which claims the benefit of priority under 35 U.S.C. §119(e) from U.S. Provisional Application No. 60/787,775 filed Mar. 31, 2006, and U.S. Provisional Application No. 60/871,864, filed Dec. 26, 2006, the entire contents of which are incorporated herein by reference.

BACKGROUND OF THE INVENTION

The present application is related to implants for use in or near the nasolacrimal drainage system, with embodiments providing canalicular implants, lacrimal sac implants, punctal plugs and punctal plugs with drug delivery capabilities.

A variety of challenges face patients and physicians in the area of ocular drug delivery. In particular, the repetitive nature of the therapies (multiple injections, instilling multiple eye drop regimens per day), the associated costs, and the lack of patient compliance may significantly impact the efficacy of the therapies available, leading to reduction in vision and many times blindness.

Patient compliance in taking the medications, for example instilling the eye drops, can be erratic, and in some cases, patients may not follow the directed treatment regime. Lack of compliance can include, failure to instill the drops, ineffective technique (instilling less than required), excessive use of the drops (leading to systemic side effects), and use of non-prescribed drops or failure to follow the treatment regime requiring multiple types of drops. Many of the medications may require the patient to instill them up to 4 times a day.

In addition to compliance, the cost of at least some eye drop medications is increasing, leading some patients on limited incomes to be faced with the choice of buying basic necessities or instead getting their prescriptions filled. Many times insurance does not cover the total cost of the prescribed eye drop medication, or in some cases eye drops containing multiple different medications.

Further, in many cases, topically applied medications have a peak ocular effect within about two hours, after which additional applications of the medications should be performed to maintain the therapeutic benefit. In addition, inconsistency in self-administered or ingested medication regimes can result in a suboptimal therapy. PCT Publication WO 06/014434 (Lazar), which is incorporated herein by reference in its entirety, may be relevant to these and/or other issues associated with eye drops.

One promising approach to ocular drug delivery is to place an implant that releases a drug in tissue near the eye. Although this approach can offer some improvement over eye drops, some potential problems of this approach may include implantation of the implant at the desire tissue location, retention of the implant at the desired tissue location, and sustaining release of the drug at the desired therapeutic level for an extended period of time. For example in the case of glaucoma treatment, undetected and premature loss of an implant can result in no drug being delivered, and the patient can potentially suffer a reduction in vision, possibly even blindness.

In light of the above, it would be desirable to provide improved drug delivery implants that overcome at least some of the above mentioned shortcomings.

BRIEF SUMMARY OF THE INVENTION

The present invention provides implant devices, systems and methods for delivery of a therapeutic agent from a punctum of a patient ocular tissues.

In a first aspect, embodiments of the present invention provide an implant for insertion into a punctum of a patient. The punctum provides a flow path for a tear fluid from an eye to a canalicular lumen. The implant comprises a body. The body has a distal end, a proximal end, and an axis therebetween. The distal end of the body is insertable distally through the punctum into the canalicular lumen. The body comprises a therapeutic agent included within an agent matrix drug core. Exposure of the agent matrix to the tear fluid effects an effective therapeutic agent release into the tear fluid over a sustained period. The body has a sheath disposed over the agent matrix to inhibit release of the agent away from the proximal end. The body also has an outer surface configured to engage luminal wall tissues so as to inhibit expulsion when disposed therein.

In some embodiments, the agent matrix comprises a non-bioabsorbable polymer, for example silicone in a non-homogenous mixture with the agent. The non-homogeneous mixture may comprise a silicone matrix saturated with the therapeutic agent and inclusions of the therapeutic agent.

In many embodiments, the outer surface of the body can be disposed on the sheath, and the outer surface may define a body shape that inhibits expulsion of the body from the punctum. The body may further comprise a support structure over the agent matrix. The support structure may define the outer surface and be configured to inhibit expulsion of the body from the punctum. In specific embodiments, the support structure receives the sheath and agent matrix drug core therein, and inhibits inadvertent expulsion of the agent matrix in use. The support structure can comprise a helical coil. The support structure may have a receptacle therein, and the receptacle may fittingly receive the sheath and agent matrix therein so as to allow unrestricted fluid communication between the proximal end and the tear film in use. The outer surface may expand radially when released within the punctum, and the radial expansion may inhibits the expulsion from the punctum.

In specific embodiments, the agent comprises a prostaglandin analogue, and the extended period comprises at least 3 months.

In many embodiments, an implant for insertion into a patient is provided. The patient having path for tear fluid associated with an eye, and the implant comprises a body. The body can comprise a therapeutic agent and a support structure. The body can be configured to, when implanted at a target location along the tear fluid path, release a quantity of the therapeutic agent into the tear fluid each day for a sustained release period of days. The quantity can be significantly less than a recommended daily drop-administered quantity of the therapeutic agent. For example, the quantity can be less than 10% of the recommended drop-administered quantity. In specific embodiments, the quantity can be less than 5% of the recommended drop-administered quantity.

In many embodiments, the period comprises at least three weeks and may comprise at least three months. The therapeutic agent may comprise Timolol maleate. The body may comprise in a range from about 270 μg to about 1350 μg of the therapeutic agent. The quantity released each day can be in a range from about 20 μg to about 135 μg.

In many embodiments, the therapeutic agent may comprise a prostaglandin analogue, for example Latanoprost and/or Bimatoprost, and the body can comprise therapeutic agent in a range from about 3 μg to about 135 μg. The quantity can be in a range from about 5 ng to about 500 ng. In specific embodiments, the body may comprise therapeutic agent in a range from about 5 μg to about 30 μg, and the quantity can be in a range from about 10 ng to 150 ng.

In another aspect, embodiments of the present invention provide a method of delivering a therapeutic agent to an eye having associated tear fluid. The method comprises placing a drug core in a canaliculus of the eye. The drug core comprises a matrix and inclusions of the therapeutic agent within the matrix. A portion of the drug core is exposed to the tear. The therapeutic agent is released to the tear of the eye. The therapeutic agent dissolves into the matrix such that the matrix remains substantially saturated with the therapeutic agent while the therapeutic agent is released through the exposed portion at therapeutic levels over a sustained period.

In many embodiments, a rate of release is substantially determined by solubility of the agent in the core, the solubility of the agent in the tear and an area of the exposed portion. The drug can be released through the exposed portion at therapeutic levels for about 90 days. The therapeutic agent may comprise a prostaglandin analogue, and the inclusions of the therapeutic agent comprise an oil. The therapeutic agent can be encapsulated within the matrix, and the matrix may comprise a non-bioabsorbable polymer.

In many embodiments, the therapeutic agent has a solubility in water of less than about 0.03% percent by weight. The therapeutic agent can be released at therapeutic levels in response to a surfactant of the tear. A sheath may be disposed over the core to define the exposed portion, and the exposed portion oriented toward the eye on a proximal end of the core.

In many embodiments, a punctal plug to treat glaucoma is provided. The plug comprises a body no more than about 2.0 mm across. When inserted in the punctum for 35 days the body delivers at least a therapeutic quantity of therapeutic agent each day of the 35 days. In some embodiments, the body no more than about 2.0 mm across comprises a cross sectional size no more than about 1.0 mm across while inserted into the patient. In specific embodiments, the body comprises a drug core and the therapeutic agent is delivered from the drug core. The drug core may be no more than about 1 mm across, and the body may be no more than about 2 mm in length.

In many embodiments, a method of treating glaucoma is provided with a punctal plug, The method comprises eluting at least 10 ng per day of a therapeutic agent from the punctal plug for at least 90 days. In specific embodiments, the therapeutic agent comprises at least one of Bimatoprost or Latanoprost. The therapeutic agent may have a solubility in water no more than about 0.03% by weight.

In many embodiments, a punctal plug to treat glaucoma is provided, the plug comprises a body. The body comprises a therapeutic agent, and the body is adapted to release the therapeutic agent at therapeutic levels in response to a surfactant of the eye. In specific embodiments, the therapeutic agent has a solubility in water no more than about 0.03% by weight. The therapeutic agent may comprise cyclosporin.

In many embodiments, a punctal plug to treat glaucoma is provided. The plug comprises a plug body. The body comprises a therapeutic agent. The body is adapted to release from about 80 to 120 ng of the therapeutic agent into a tear of the eye for at least about 20 days. In specific embodiments, the therapeutic agent may comprise at least one of Bimatoprost or Latanoprost.

In some embodiments, a punctal plug to treat glaucoma is provided. The punctal plug comprises a body. The body comprises therapeutic agent stored within a volume no more than about 0.02 cm$^3$. The body is adapted to deliver therapeutic levels of the therapeutic agent for at least about 1 month. In specific embodiments, the body is adapted to deliver the therapeutic agent at therapeutic levels for at least about 3 months. The body can be adapted to deliver the therapeutic agent with a substantially zero order release rate for the at least one month.

In some embodiments, composition of matter to treat glaucoma of an eye having an associated tear is provided. The composition comprises inclusions. The inclusions comprise a concentrated form of a therapeutic agent. The therapeutic agent comprises a solubility in water no more than about 0.03% by weight. A silicone matrix encapsulates the inclusions. The therapeutic agent is soluble in the silicone matrix to release the therapeutic agent from the silicon matrix into the tear at therapeutic levels. In specific embodiments, the therapeutic agent inclusions are encapsulated within the silicon matrix comprise an inhomogeneous mixture of the inclusions encapsulated within the silicon matrix. The inclusions can comprise Latanoprost oil.

BRIEF DESCRIPTION OF THE DRAWINGS

FIGS. 7D and 7E show dependence of the rate of elution on exposed surface area of the drug core for the three core diameters and the three concentrations as in FIGS. 7A and 7B Latanoprost at day 1 and day 14, respectively, according to embodiments of the present invention;

FIG. 8A shows elution profiles of cyclosporine from drug cores into a buffer solution with surfactant and a buffer solution with surfactant, according to embodiments of the present invention;

FIG. 10A shows profiles of elution of Latanoprost from the cores for four formulations of Latanoprost according to embodiments of the present invention.

DETAILED DESCRIPTION OF THE INVENTION

Figure 1:
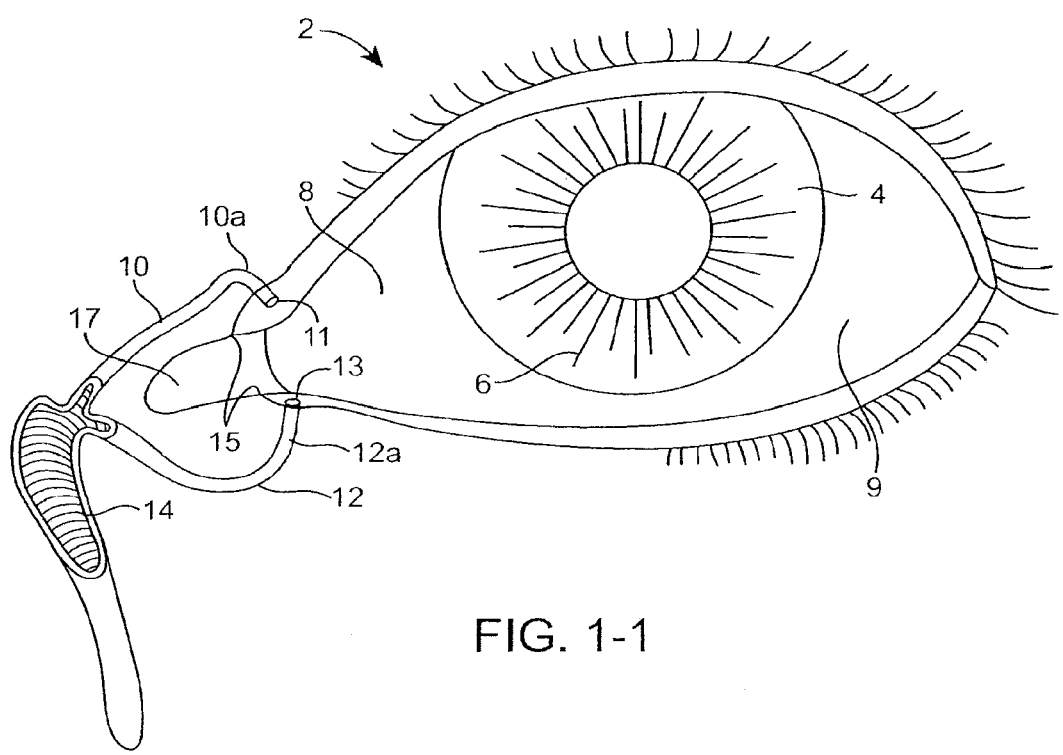
FIGS. 1-1 and 1-2 show anatomical tissue structures of the eye suitable for use with implants, according to embodiments of the present invention.
Figures 1, 2:
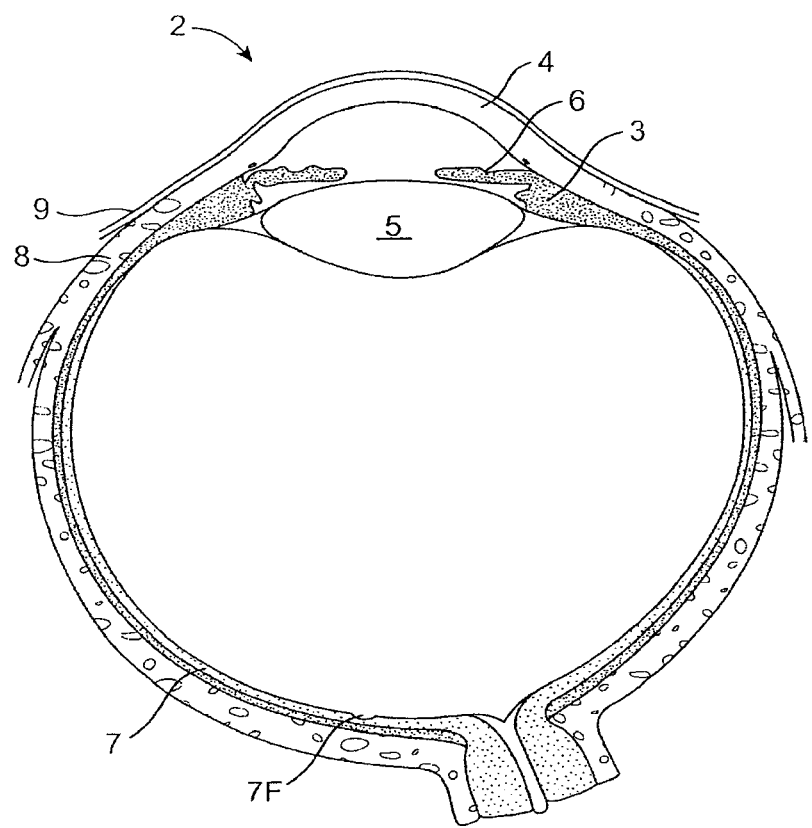

FIGS. 1-1 and 1-2 show anatomical tissue structures of an eye 2 suitable for treatment with implants, according to an embodiment of the present invention. Eye 2 includes a cornea 4 and an iris 6. A sclera 8 surrounds cornea 4 and iris 6 and appears white. A conjunctival layer 9 is substantially transparent and disposed over sclera 8. A crystalline lens 5 is located within the eye. A retina 7 is located near the back of eye 2 and is generally sensitive to light. Retina 7 includes a fovea 7F that provides high visual acuity and color vision. Cornea 4 and lens 5 refract light to form an image on fovea 7F and retina 7. The optical power of cornea 4 and lens 5 contribute to the formation of images on fovea 7F and retina 7. The relative locations of cornea 4, lens 5 and fovea 7F are also important to image quality. For example, if the axial length of eye 2 from cornea 4 to retina 7F is large, eye 2 can be myopic. Also, during accommodation, lens 5 moves toward cornea 4 to provide good near vision of objects proximal to the eye.

The anatomical tissue structures shown in FIG. 1-1 also include the lacrimal system, which includes an upper canaliculus 10 and a lower canaliculus 12, collectively the canaliculae, and the naso-lacrimal duct or sac 14. The upper and lower canaliculae terminate in an upper punctum 11 and a lower punctum 13, also referred to as punctal apertures. The punctal apertures are situated on a slight elevation at the medial end of the lid margin at the junction 15 of the ciliary and lacrimal portions near the medial canthus 17. The punctal apertures are round or slightly ovoid openings surrounded by a connective ring of tissue. Each of the punctal openings 11, 13 leads into a vertical portion 10a, 12a of the respective canaliculus before turning horizontally to join its other canaliculus at the entrance of a lacrimal sac 14. The canaliculae are tubular and lined by stratified squamous epithelium surrounded by elastic tissue which permits the canaliculus to be dilated.

Figure 1A:
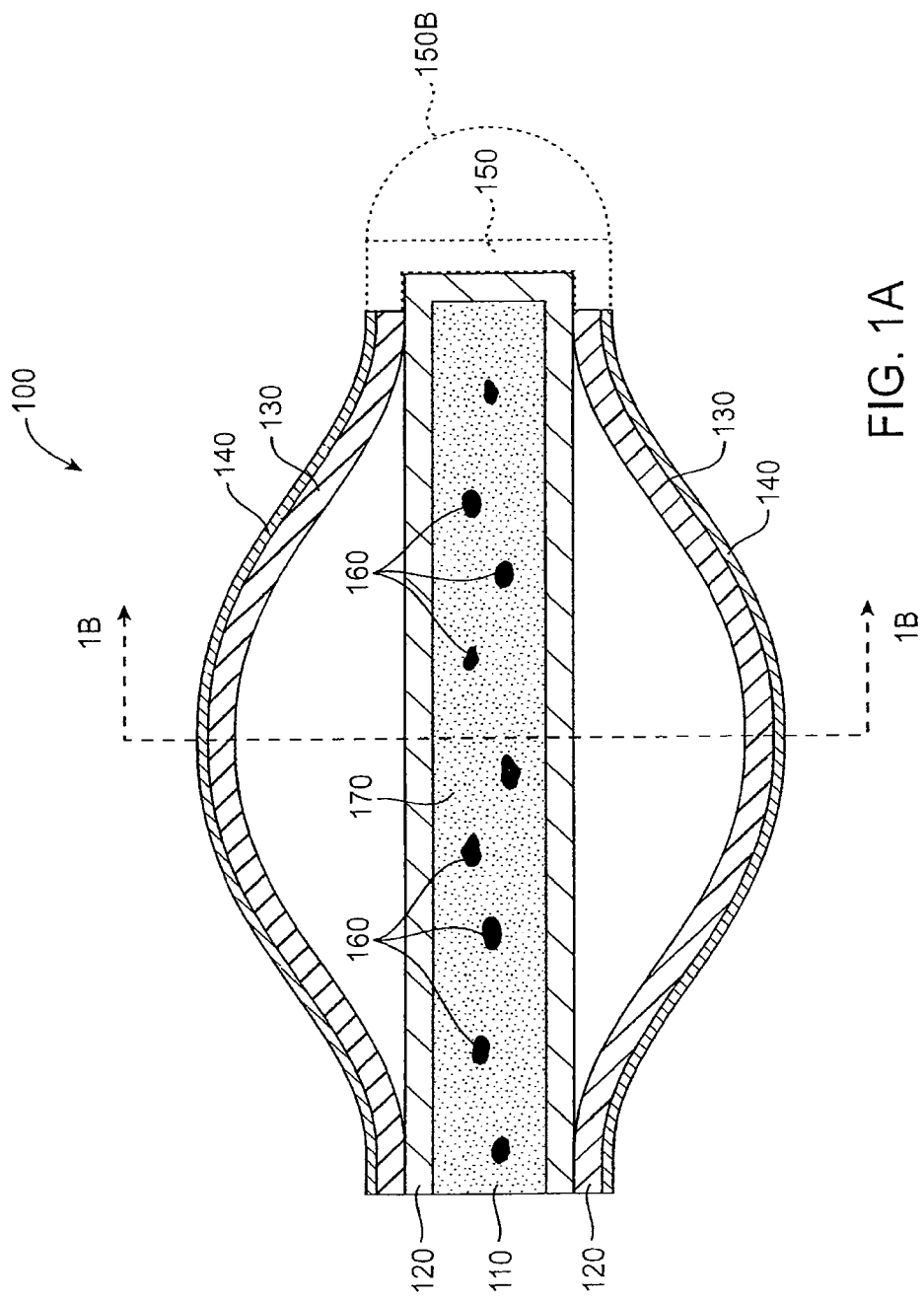
FIG. 1A shows a top cross sectional view of a sustained release implant to treat an optical defect of an eye, according to an embodiment of the present invention.

FIG. 1A shows a top cross sectional view of a sustained release implant 100 to treat an optical defect of an eye, according to embodiments of the present invention. Implant 100 includes a drug core 110. Drug core 110 is an implantable structure that retains a therapeutic agent. Drug core 110 comprises a matrix 170 that contains inclusions 160 of therapeutic agent. Inclusions 160 will often comprise a concentrated form of the therapeutic agent, for example a crystalline form of the therapeutic agent, and the therapeutic agent may over time dissolve into matrix 170 of drug core 110. Matrix 170 can comprise a silicone matrix or the like, and the mixture of therapeutic agent within matrix 170 can be non-homogeneous. In many embodiments, the non-homogenous mixture comprises a silicone matrix portion that is saturated with the therapeutic agent and an inclusions portion comprising inclusions of the therapeutic agent, such that the non-homogenous mixture comprises a multiphase non-homogenous mixture. In some embodiments, inclusions 160 comprise droplets of an oil of the therapeutic agent, for example Latanoprost oil. In some embodiments, inclusions 160 may comprise particles of the therapeutic agent, for example solid Bimatoprost particles in crystalline form. In many embodiments, matrix 170 encapsulates inclusions 160, and inclusions 160 may comprise microparticles have dimensions from about 1 μm to about 100 μm. The encapsulated inclusions dissolve into the surrounding solid matrix, for example silicone, that encapsulates the micro particles such that matrix 170 is substantially saturated with the therapeutic agent while the therapeutic agent is released from the core.

Drug core 110 is surrounded by a sheath body 120. Sheath body 120 is can be substantially impermeable to the therapeutic agent, so that the therapeutic agent is often released from an exposed surface on an end of drug core 110 that is not covered with sheath body 120. A retention structure 130 is connected to drug core 110 and sheath body 120. Retention structure 130 is shaped to retain the implant in a hollow tissue structure, for example, a punctum of a canaliculus as described above.

An occlusive element 140 is disposed on and around retention structure 130. Occlusive element 140 is impermeable to tear flow and occludes the hollow tissue structure and may also serve to protect tissues of the tissue structure from retention structure 130 by providing a more benign tissue-engaging surface. Sheath body 120 includes a sheath body portion 150 that connects to retention structure 130 to retain sheath body 120 and drug core 110. Sheath body portion 150 can include a stop to limit movement of sheath body 120 and drug core 110. In many embodiments, sheath body portion 150 can be formed with a bulbous tip 150B. Bulbous tip 150B can comprise a convex rounded external portion that provides atraumatic entry upon introduction into the canaliculus. In many embodiments, sheath body portion 150B can be integral with occlusive element 140.

Figure 1B:
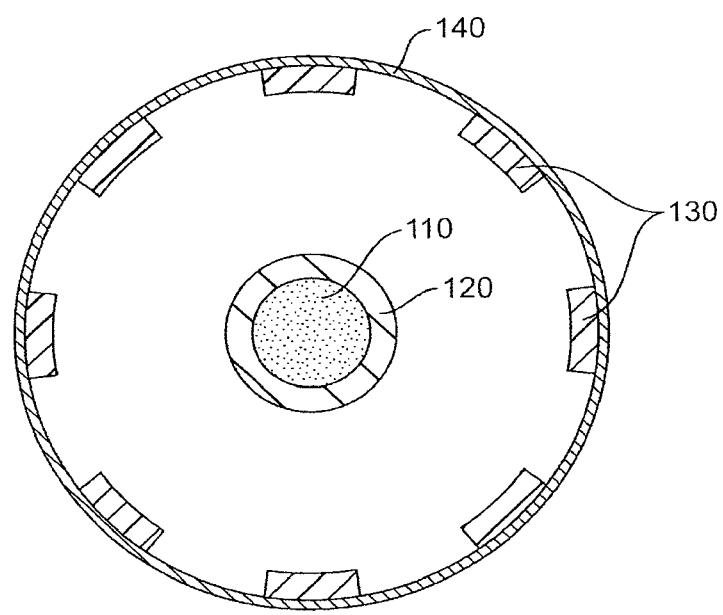
FIG. 1B shows a side cross sectional view of the sustained release implant of FIG. 1A.

FIG. 1B shows a side cross sectional view of the sustained release implant of FIG. 1A. Drug core 110 is cylindrical and shown with a circular cross-section. Sheath body 120 comprises an annular portion disposed on drug core 110. Retention structure 130 comprises several longitudinal struts 131. Longitudinal struts 131 are connected together near the ends of the retention structure. Although longitudinal struts are shown, circumferential struts can also be used. Occlusive element 140 is supported by and disposed over longitudinal struts 131 of retention structure 130 and may comprise a radially expandable membrane or the like.

Figure 1C:
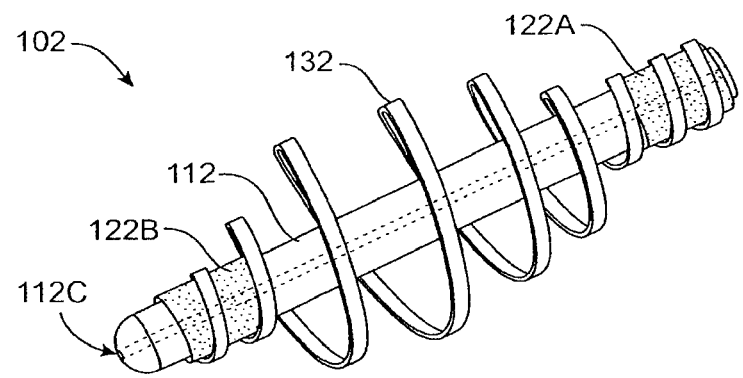
FIG. 1C shows a perspective view of a sustained release implant with a coil retention structure, according to an embodiment of the present invention.

FIG. 1C shows a perspective view of a sustained release implant 102 with a coil retention structure 132, according to an embodiment of the present invention. Retention structure 132 comprises a coil and retains a drug core 112. A lumen, for example channel 112C, may extend through the drug core 112 to permit tear flow through the lumen for the delivery of therapeutic agent for nasal and systemic applications of the therapeutic agent. In addition or in combination with channel 112C, retention structure 132 and core 112 can be sized to permit tear flow around the drug core and sheath body while the retention element holds tissue of the canaliculus away from the drug core. Drug core 112 may be partially covered. The sheath body comprises a first component 122A that covers a first end of drug cove 112 and a second component 122B that covers a second end of the drug core. An occlusive element can be placed over the retention structure and/or the retention structure can be dip coated as described above.

Figure 1D:
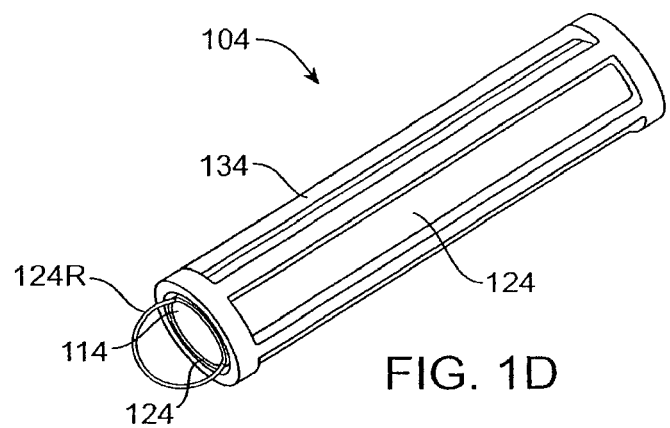
FIG. 1D shows a perspective view of a sustained release implant with a retention structure comprising struts, according to an embodiment of the present invention.

FIG. 1D shows a perspective view of a sustained release implant 104 with a retention structure 134 comprising struts, according to an embodiment of the present invention. Retention structure 134 comprises longitudinal struts and retains a drug core 114. Drug core 114 is covered with a sheath body 124 over most of drug core 114. The drug core releases therapeutic agent through an exposed end and sheath body 124 is annular over most of the drug core as described above. An occlusive element can be placed over the retention structure or the retention structure can be dip coated as described above. A protrusion that can be engaged with an instrument, for example a hook, a loop, a suture, or ring 124R, can extend from sheath body 124 to permit removal of the drug core and sheath body together so as to facilitate replacement of the sheath body and drug core while the retention structure remains implanted in the canaliculus. In some embodiments, a protrusion that can be engaged with an instrument comprising hook, a loop, a suture or a ring, can extend from retention structure 134 to permit removal of the sustained release implant by removing the retention structure with the protrusion, drug core and sheath body.

Figure 1E:
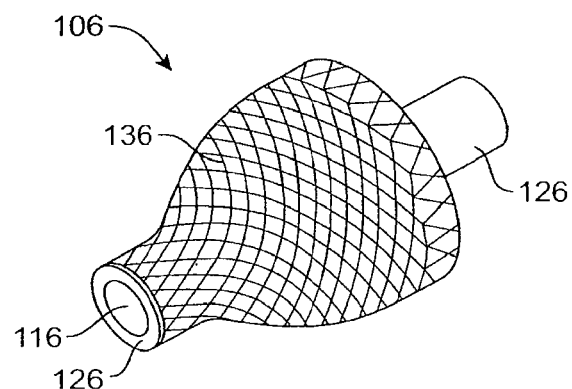
FIG. 1E shows a perspective view of a sustained release implant with a cage retention structure, according to an embodiment of the present invention.

FIG. 1E shows a perspective view of a sustained release implant 106 with a cage retention structure 136, according to an embodiment of the present invention. Retention structure 136 comprises several connected strands of metal and retains a drug core 116. Drug core 116 is covered with a sheath body 126 over most of drug core 116. The drug core releases therapeutic agent through an exposed end and sheath body 126 is annular over most of the drug core as described above. An occlusive element can be placed over the retention structure or the retention structure can be dip coated as described above.

Figure 1F:
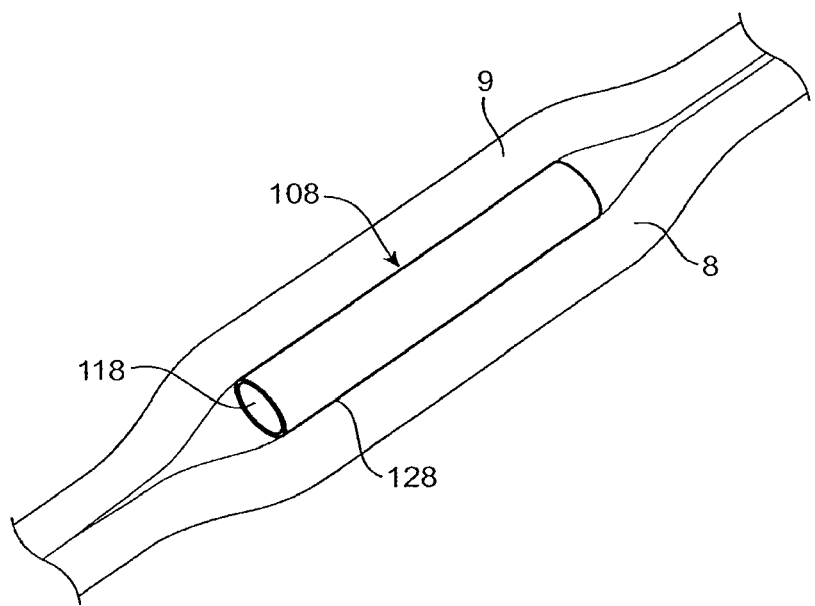
FIG. 1F shows a perspective view of a sustained release implant comprising a core and sheath, according to an embodiment of the present invention.

FIG. 1F shows a perspective view of a sustained release implant comprising a core and sheath, according to an embodiment of the present invention. Drug core 118 is covered with a sheath body 128 over most of drug core 118. The drug core releases therapeutic agent through an exposed end and sheath body 128 is annular over most of the drug core as described above.

The rate of therapeutic agent release is controlled by the surface area of the exposed drug core and materials included within drug core 118. In many embodiments, the rate of elution of the therapeutic agent is strongly and substantially related to the exposed surface area of the drug core and weakly dependent on the concentration of drug disposed in the inclusions in the drug core.

For circular exposed surfaces the rate of elution is strongly dependent on the diameter of the exposed surface, for example the diameter of an exposed drug core surface near an end of a cylindrical drug core. Such an implant can be implanted in ocular tissues, for example below conjunctival tissue layer 9 of the eye and either above sclera tissue layer 8, as shown in FIG. 1F, or only partially within the scleral tissue layer so as not to penetrate the scleral tissue. It should be noted that drug core 118 can be used with any of the retention structures and occlusive elements as described herein.

In an embodiment, the drug core is implanted between sclera 8 and conjunctiva 9 without sheath body 128. In this embodiment without the sheath body, the physical characteristics of the drug core can be adjusted to compensate for the increased exposed surface of drug core, for example by reducing the concentration of dissolved therapeutic agent in the drug core matrix as described herein.

Figure 1G:
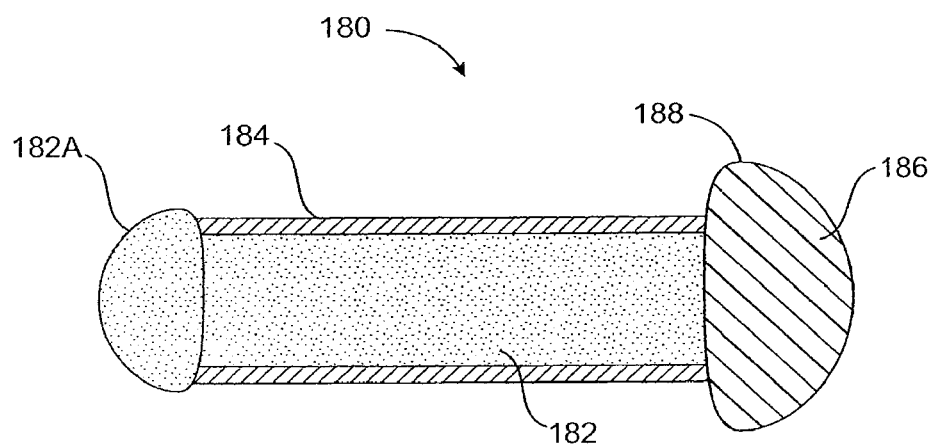
FIG. 1G schematically illustrates a sustained release implant comprising a flow restricting retention element, a core and a sheath, according to an embodiment of the present invention.

FIG. 1G schematically illustrates a sustained release implant 180 comprising a flow restricting retention structure 186, a core 182 and a sheath 184, according to an embodiment of the present invention. Sheath body 184 can at least partially cover drug core 182. Drug core 182 may contain inclusions of the therapeutic agent therein to provide a sustained release of the therapeutic agent. Drug core 182 can include an exposed convex surface area 182A. Exposed convex surface area 182A may provide an increased surface area to release the therapeutic agent.

An occlusive element 188 can be disposed over retention structure 186 to block the flow of tear through the canaliculus. In many embodiments, retention structure 186 can be located within occlusive structure 188 to provide the occlusive element integrated with the retention structure.

Flow restricting retention structure 186 and occlusive element 188 can be sized to block tear flow through the canaliculus.

The cores and sheath bodies described herein can be implanted in a variety of tissues in several ways. Many of the cores and sheaths described herein, in particular the structures described with reference to FIGS. 2A to 2J can be implanted alone as punctal plugs.

Alternatively, many of the cores and sheath bodies described herein can comprise a drug core, sheath body, and/or the like so as to be implanted with the retention structures and occlusive elements described herein.

Figure 2A:
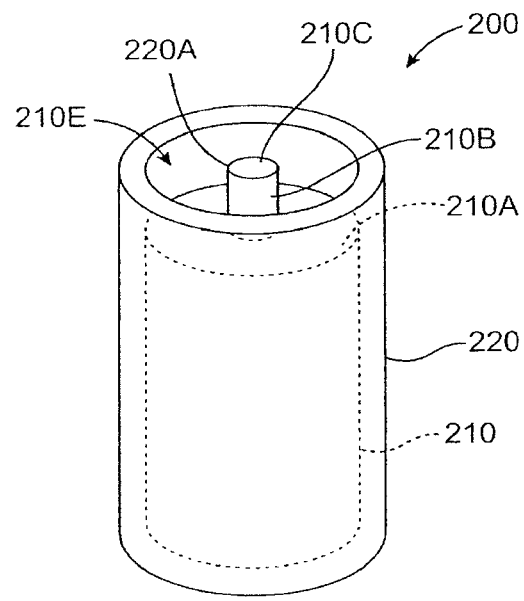
FIG. 2A shows a cross sectional view of a sustained release implant with core comprising an enlarged exposed surface area, according to an embodiment of the present invention.

FIG. 2A shows a cross sectional view of a sustained release implant 200 with core comprising an enlarged exposed surface area, according to an embodiment of the present invention. A drug core 210 is covered with a sheath body 220. Sheath body 220 includes an opening 220A. Opening 220 has a diameter that approximates the maximum cross sectional diameter of drug core 210. Drug core 210 includes an exposed surface 210E, also referred to as an active surface. Exposed surface 210E includes 3 surfaces: an annular surface 210A, a cylindrical surface 210B and an end surface 210C. Annular surface 210A has an outer diameter that approximates the maximum cross sectional diameter of core 210 and an inner diameter that approximates the outer diameter of cylindrical surface 210B. End surface 210C has a diameter that matches the diameter of cylindrical surface 210B. The surface area of exposed surface 210E is the sum of the areas of annular surface 210A, cylindrical surface 210B and end surface 210C.

The surface area may be increased by the size of cylindrical surface area 210B that extends longitudinally along an axis of core 210.

Figure 2B:
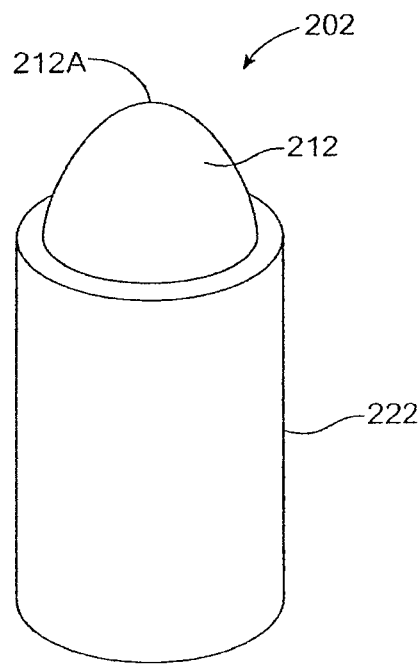
FIG. 2B shows a cross sectional view of a sustained release implant with a core comprising an enlarged exposed surface area, according to an embodiment of the present invention.

FIG. 2B shows a cross sectional view of a sustained release implant 202 with a core 212 comprising an enlarged exposed surface area 212A, according to an embodiment of the present invention. A sheath body 222 extends over core 212. The treatment agent can be released from the core as described above. Exposed surface area 212A is approximately conical, can be ellipsoidal or spherical, and extends outward from the sheath body to increase the exposed surface area of drug core 212.

Figure 2C:
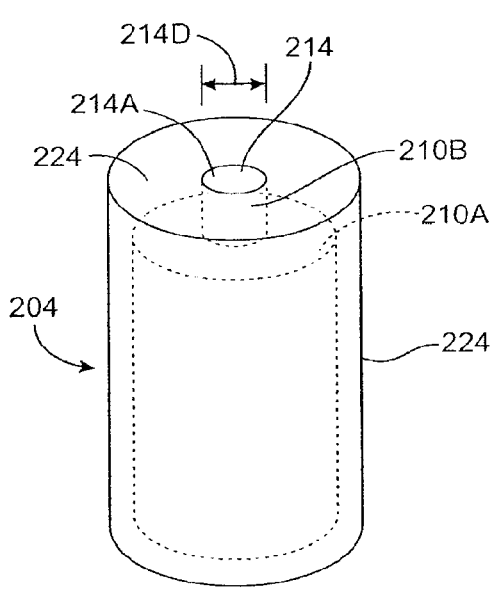
FIGS. 2C and 2D show perspective view and cross sectional views, respectively, of a sustained release implant with a core comprising a reduced exposed surface area, according to an embodiment of the present invention.
Figure 2D:
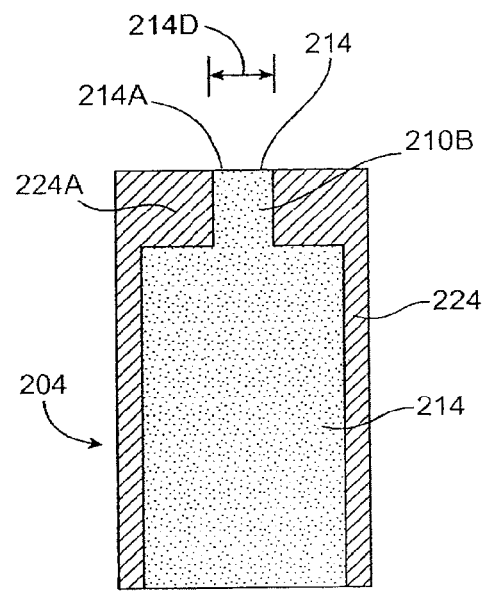

FIGS. 2C and 2D show perspective and cross sectional views, respectively, of a sustained release implant 204 with a drug core 214 comprising a reduced exposed surface area 214A, according to an embodiment of the present invention. Drug core 214 is enclosed within a sheath body 224. Sheath body 22 includes an annular end portion 224A that defines an opening through which drug core 214 extends. Drug core 214 includes an exposed surface 214A that releases the therapeutic agent. Exposed surface 214A has a diameter 214D that is less than a maximum dimension, for example a maximum diameter, across drug core 214.

Figure 2E:
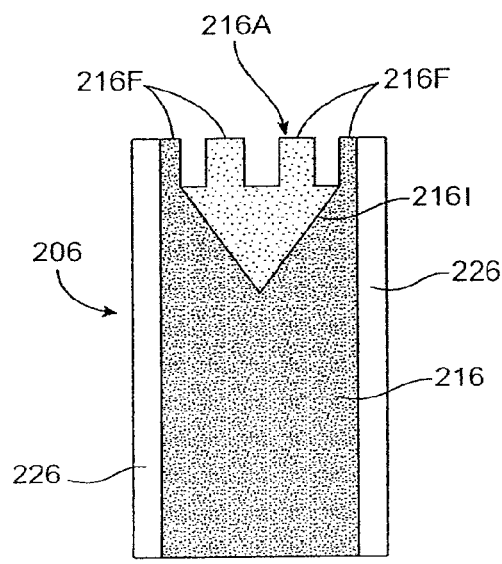
FIG. 2E shows a cross sectional view of a sustained release implant with a core comprising an enlarged exposed surface area with an indentation and castellation, according to an embodiment of the present invention.

FIG. 2E shows a cross sectional view of a sustained release implant 206 with a drug core 216 comprising an enlarged exposed surface area 216A with castellation extending therefrom, according to an embodiment of the present invention. The castellation includes several spaced apart fingers 216F to provide increased surface area of the exposed surface 216A.

In addition to increased surface area provided by castellation, drug core 216 may also include an indentation 216I. Indentation 216I may have the shape of an inverted cone. Core 216 is covered with a sheath body 226. Sheath body 226 is open on one end to provide an exposed surface 216A on drug core 216. Sheath body 226 also includes fingers and has a castellation pattern that matches core 216.

Figure 2F:
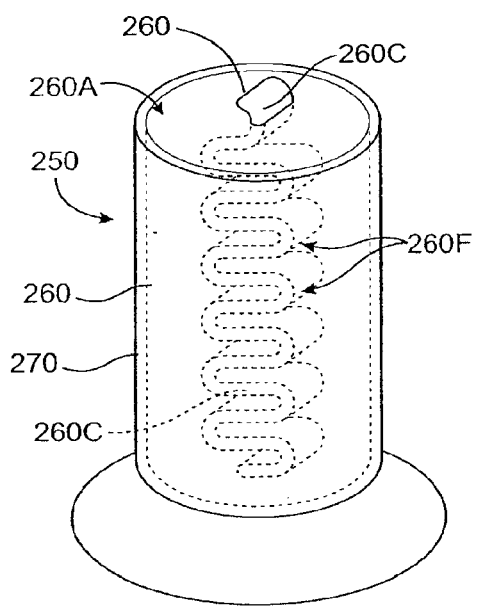
FIG. 2F shows a perspective view of a sustained release implant comprising a core with folds, according to an embodiment of the present invention.

FIG. 2F shows a perspective view of a sustained release implant 250 comprising a core with folds, according to an embodiment of the present invention. Implant 250 includes a core 260 and a sheath body 270. Core 260 has an exposed surface 260A on the end of the core that permits drug migration to the surrounding tear or tear film fluid. Core 260 also includes folds 260F. Folds 260F increase the surface area of core that is exposed to the surrounding fluid tear or tear film fluid. With this increase in exposed surface area, folds 260F increase migration of the therapeutic agent from core 260 into the tear or tear film fluid and target treatment area.

Folds 260F are formed so that a channel 260C is formed in core 260. Channel 260C connects to the end of the core to an opening in exposed surface 260A and provides for the migration of treatment agent. Thus, the total exposed surface area of core 260 includes exposed surface 260A that is directly exposed to the tear or tear film fluid and the surfaces of folds 260F that are exposed to the tear or tear film fluids via connection of channel 260C with exposed surface 260A and the tear or tear film fluid.

Figure 2G:
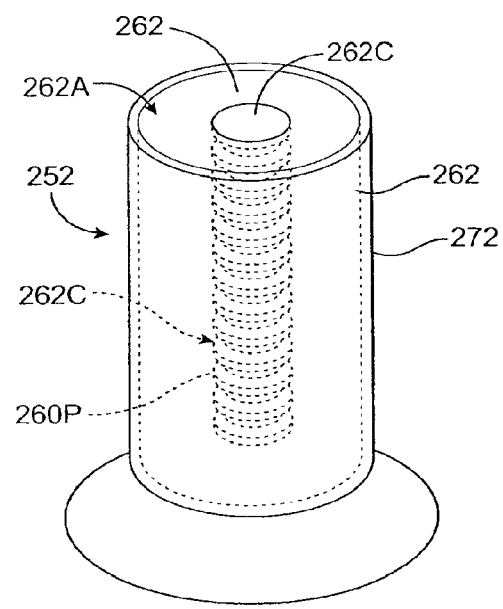
FIG. 2G shows a perspective view of a sustained release implant with a core comprising a channel with an internal porous surface, according to an embodiment of the present invention.

FIG. 2G shows a perspective view of a sustained release implant with a core comprising a channel with an internal porous surface, according to an embodiment of the present invention.

Implant 252 includes a core 262 and sheath body 272. Core 262 has an exposed surface 262A on the end of the core that permits drug migration to the surrounding tear or tear film fluid. Core 262 also includes a channel 262C. Channel 262C increases the surface area of the channel with a porous internal surface 262P formed on the inside of the channel against the core. Channel 262C extends to the end of the core near exposed surface 262A of the core. The surface area of core that is exposed to the surrounding tear or tear film fluid can include the inside of core 262 that is exposed to channel 262C. This increase in exposed surface area can increase migration of the therapeutic agent from core 262 into the tear or tear film fluid and target treatment area. Thus, the total exposed surface area of core 262 can include exposed surface 260A that is directly exposed to the tear or tear film fluid and porous internal surface 262P that is exposed to the tear or tear film fluids via connection of channel 262C with exposed surface 262A and the tear or tear film fluid.

Figure 2H:
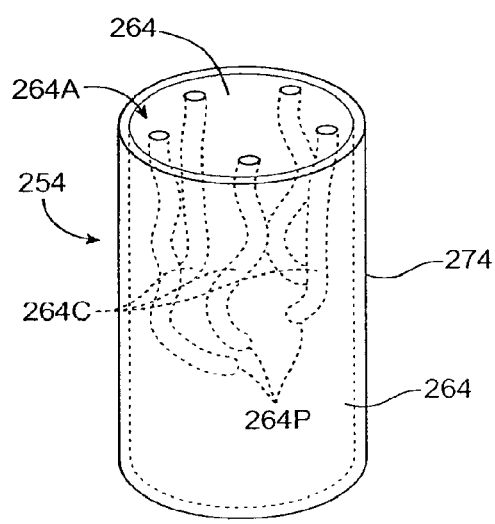
FIG. 2H shows a perspective view of a sustained release implant with a core comprising porous channels to increase drug migration, according to an embodiment of the invention.

FIG. 2H shows a perspective view of a sustained release implant 254 with a core 264 comprising channels to increase drug migration, according to an embodiment of the invention. Implant 254 includes core 264 and sheath body 274. Exposed surface 264A is located on the end of core 264, although the exposed surface can be positioned at other locations. Exposed surface 264A permits drug migration to the surrounding tear or tear film fluid. Core 264 also includes channels 264C Channels 264C extend to exposed surface 264. Channels 264C are large enough that tear or tear film fluid can enter the channels and therefore increase the surface area of core 264 that is in contact with tear or tear film fluid. The surface area of the core that is exposed to the surrounding fluid tear or tear film fluid includes the inner surfaces 264P of core 262 that define channels 264C. With this increase in exposed surface area, channels 264C increase migration of the therapeutic agent from core 264 into the tear or tear film fluid and target treatment area. Thus, the total exposed surface area of core 264 includes exposed surface 264A that is directly exposed to the tear or tear film fluid and internal surface 264P that is exposed to the tear or tear film fluids via connection of channels 262C with exposed surface 264A and the tear or tear film fluid.

Figure 2I:
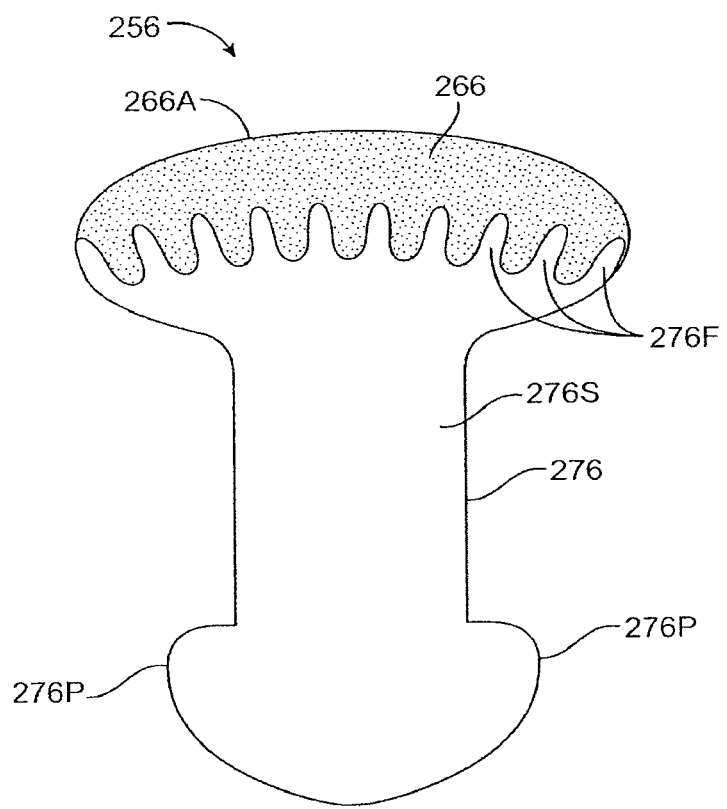
FIG. 2I shows a perspective view of a sustained release implant with a convex exposed drug core surface, according to an embodiment of the present invention.

FIG. 2I shows a perspective view of a sustained release implant 256 with a drug core 266 comprising a convex exposed surface 266A, according to an embodiment of the present invention. Drug core 266 is partially covered with a sheath body 276 that extends at least partially over drug core 266 to define convex exposed surface 266A. Sheath body 276 comprises a shaft portion 276S. Convex exposed surface 266A provides an increased exposed surface area above the sheath body. A cross sectional area of convex exposed surface 266A is larger than a cross sectional area of shaft portion 276S of sheath body 276. In addition to the larger cross sectional area, convex exposed surface 266A has a larger surface area due to the convex shape which extends outward from the core. Sheath body 276 comprises several fingers 276F that support drug core 266 in the sheath body and provide support to the drug core to hold drug core 266 in place in sheath body 276. Fingers 276F are spaced apart to permit drug migration from the core to the tear or tear film fluid between the fingers. Protrusions 276P extend outward on sheath body 276. Protrusions 276P can be pressed inward to eject drug core 266 from sheath body 276. Drug core 266 can be replaced with another drug core after an appropriate time, for example after drug core 266 has released most of the therapeutic agent.

Figure 2J:
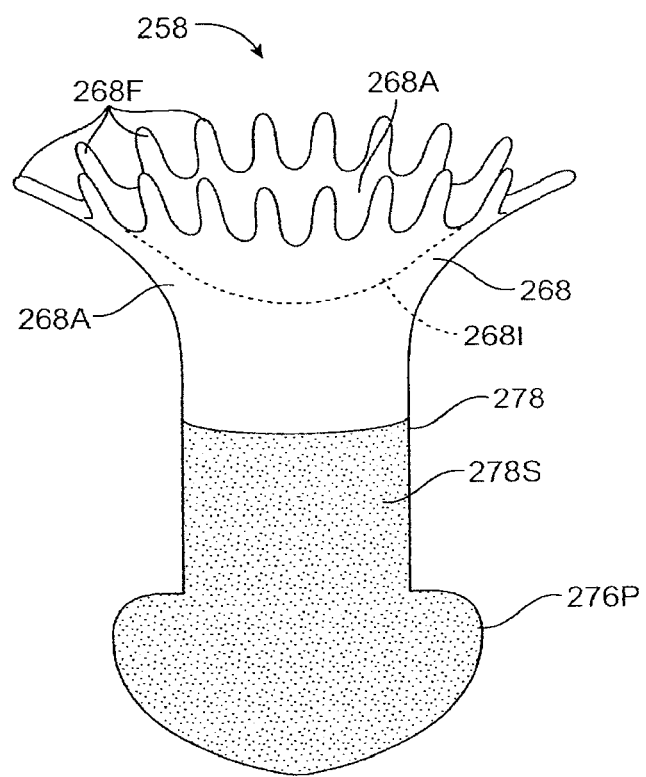
FIG. 2J shows a side view of a sustained release implant with a core comprising an exposed surface area with several soft brush-like members extending therefrom, according to an embodiment of the present invention.

FIG. 2J shows a side view of a sustained release implant 258 with a core 268 comprising an exposed surface area with several soft brush-like members 268F, according to an embodiment of the present invention. Drug core 268 is partially covered with a sheath body 278 that extends at least partially over drug core 268 to define exposed surface 268A. Sheath body 278 comprises a shaft portion 278S. Soft brush-like members 268F extend outward from drug core 268 and provide an increased exposed surface area to drug core 268. Soft brush-like members 268F are also soft and resilient and easily deflected such that these members do not cause irritation to neighboring tissue. Although drug core 268 can be made of many materials as explained above, silicone is a suitable material for the manufacture of drug core 268 comprises soft brush like members 268F. Exposed surface 268A of drug core 268 also includes an indentation 268I such that at least a portion of exposed surface 268A is concave.

Figure 2K:
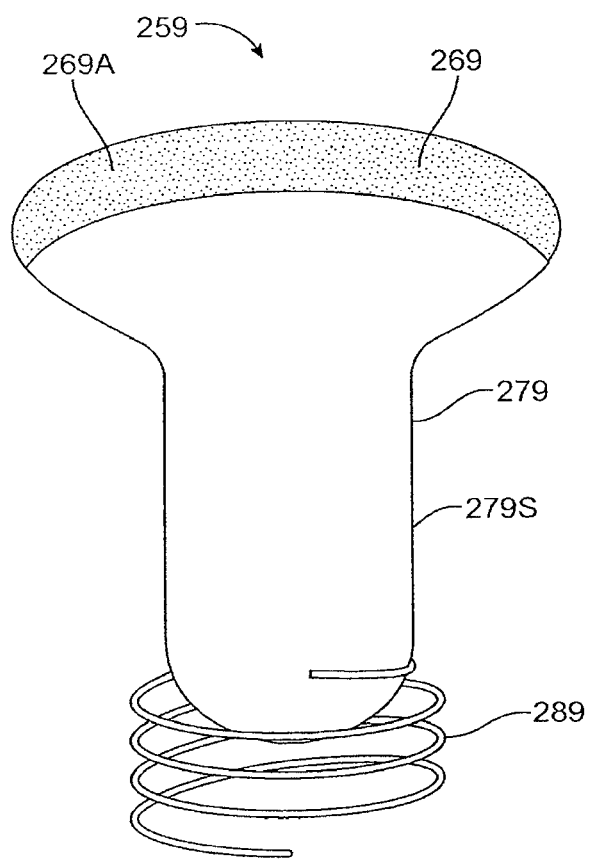
FIG. 2K shows a side view of a sustained release implant with a drug core comprising a convex exposed surface and a retention structure, according to an embodiment of the present invention.

FIG. 2K shows a side view of a sustained release implant 259 with a drug core 269 comprising a convex exposed surface 269A, according to an embodiment of the present invention. Drug core 269 is partially covered with a sheath body 279 that extends at least partially over drug core 269 to define convex exposed surface 269A. Sheath body 279 comprises a shaft portion 279S. Convex exposed surface 269 provides an increased exposed surface area above the sheath body. A cross sectional area of convex exposed surface 269A is larger than a cross sectional area of shaft portion 279S of sheath body 279. In addition to the larger cross sectional area, convex exposed surface 269A has a larger surface area due to the convex shape that extends outward on the core. A retention structure 289 can be attached to sheath body 279. Retention structure 289 can comprise any of the retention structures as describe herein, for example a coil comprising a super elastic shape memory alloy such as NITANOL®. Retention structure 289 can be dip coated to make retention structure 289 biocompatible.

Figure 2L:
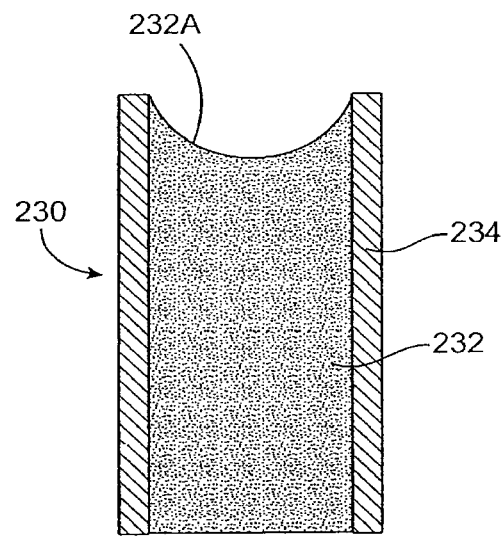
FIG. 2L shows a side view of a sustained release implant with a drug core comprising a concave indented surface to increase exposed surface area of the core, according to an embodiment of the present invention.

FIG. 2L shows a side view of a sustained release implant 230 with a drug core 232 comprising a concave indented surface 232A to increase exposed surface area of the core, according to an embodiment of the present invention. A sheath body 234 extends at least partially over drug core 232. Concave indented surface 232A is formed on an exposed end of drug core 232 to provide an increased exposed surface area of the drug core.

Figure 2M:
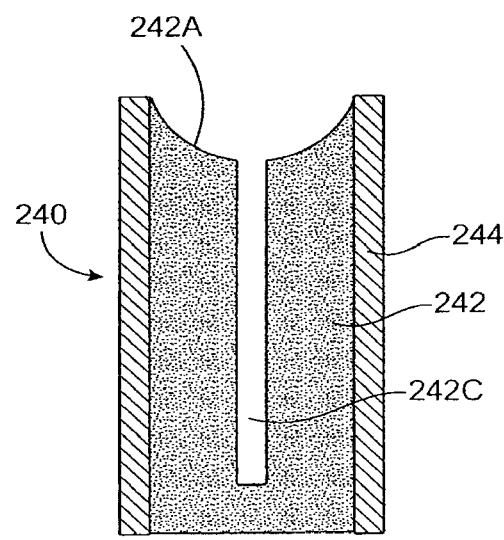
FIG. 2M shows a side view of a sustained release implant with a drug core comprising a concave surface with a channel formed therein to increase an exposed surface area of the core, according to an embodiment of the present invention.

FIG. 2M shows a side view of a sustained release implant 240 with a drug core 242 comprising a concave surface 242A with a channel 242C formed therein to increase an exposed surface area of the core, according to an embodiment of the present invention. A sheath body 244 extends at least partially over drug core 242. Concave indented surface 242A is formed on an exposed end of drug core 232 to provide an increased exposed surface area of the drug core. Channel 242C formed in drug core 242 to provide an increased exposed surface area of the drug core. Channel 242C can extend to concave indented surface 242A such that channel 242C and provide an increase in surface area of the core exposed to the tear or tear film.

Figure 3A:
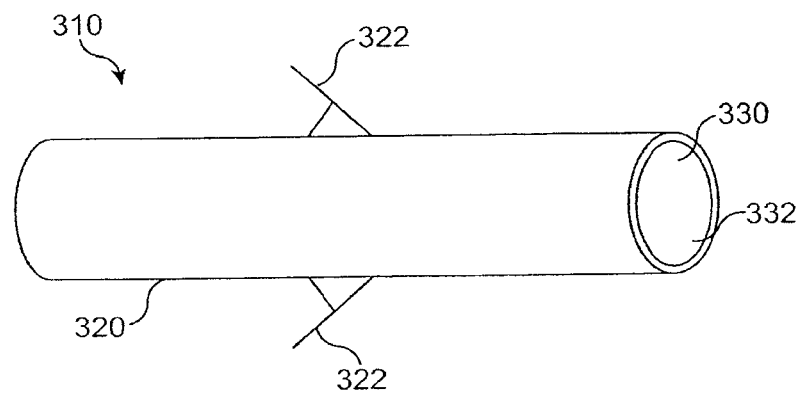
FIG. 3A shows an implant with a sheath body with extensions that attach the sheath body and core to the retention element, according to an embodiment of the present invention.

FIG. 3A shows an implant 310 comprising a sheath body 320 with extensions 322, according to an embodiment of the present invention. Extensions 322 attach sheath body 320 to the retention element to retain the core near the punctum. Sheath body 320 extends over core 330 to define an exposed surface 332 of core 330. Extensions 322 can be resilient and engage the retention element and/or occlusive element to attach the sheath body core to the retention element to retain the core near the punctum.

Figure 3B:
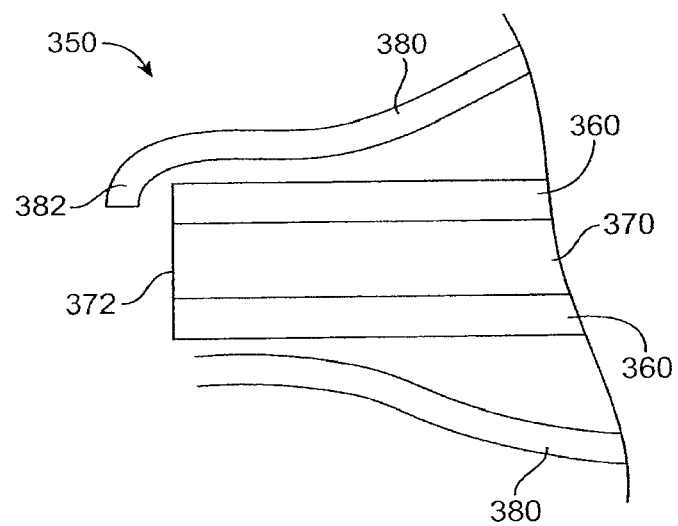
FIG. 3B shows an implant with a retention element with an extension that retains a sheath body and a core, according to an embodiment of the present invention.

FIG. 3B shows an implant 350 comprising a retention element 380 with an extension 382, according to an embodiment of the present invention. Extension 382 retains a sheath body 360 and a core 370. Sheath body 360 extends over core 370 to define an exposed surface 372 of core 370. Exposed surface 372 is disposed near the proximal end of core 370. Extension 382 extends downward to retain core 370 and sheath body 370.

Figure 4A:
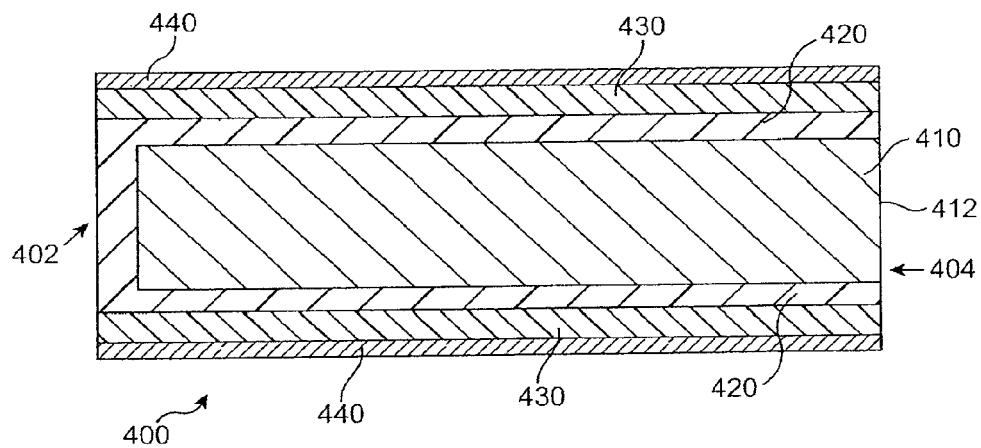
FIGS. 4A and 4B show a cross-sectional view of an implant with a retention structure that is shorter in length while in a large cross-sectional profile configuration than a small cross-sectional profile configuration, according to an embodiment of the present invention.
Figure 4B:
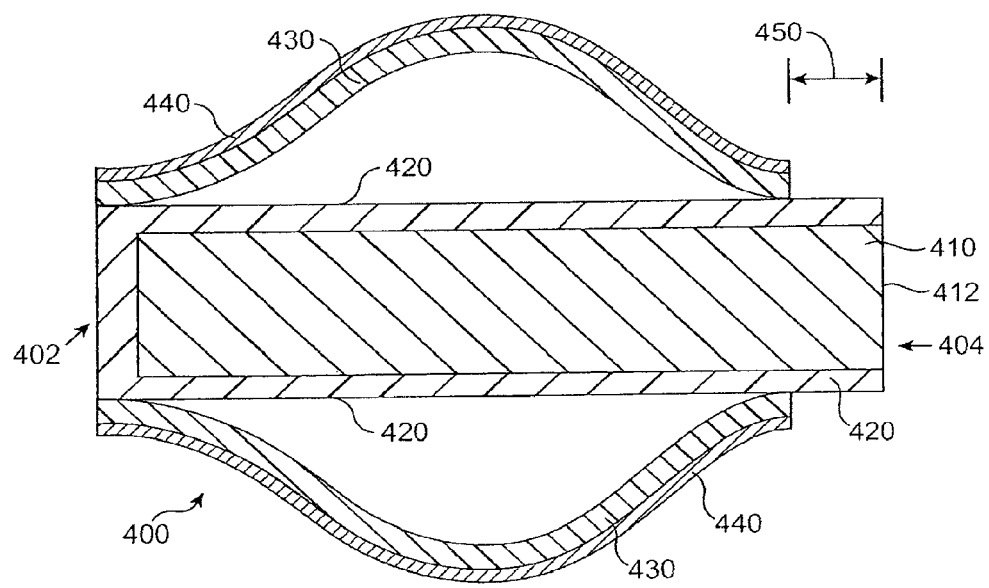

FIGS. 4A and 4B show a cross-sectional view of an implant 400 with a retention structure 430 that is shorter in length while in a large cross-sectional profile configuration than a small cross-sectional profile configuration, according to an embodiment of the present invention. Implant 400 includes a distal end 402 and a proximal end 404. Implant 400 includes a drug core 410 and a sheath body 420. Sheath body 420 at least partially covers drug core 410 and defines an exposed surface 412 of drug core 410. An occlusive element 440 can be attached to and supported by retention structure 430. Occlusive element 440 can move with retention structure 430, for example when retention element 430 expands from a small profile configuration to a large profile configuration. In many embodiments, the retention structure and occlusive element are sized to correspond to a diameter of the canaliculus, for example to match a diameter of the canaliculus or slightly larger than the canalicular diameter, so as occlude fluid flow through the canaliculus and/or anchor in the canaliculus.

As shown in FIG. 4A, retention structure 430 and occlusive element 440 are in a small profile configuration. Such a small profile configuration can occur while the occlusive element and retention structure are placed in a tip of an insertion tool and covered for deployment. Retention element 430 and occlusive element 440 extend fully along the length of sheath body 420 and drug core 410. Retention element 430 is attached to sheath body 420 near distal end 402. In many embodiments, retention structure 430 and occlusive element 440 have diameters that are sized to fit inside and slide within the canaliculus while in the small profile configuration, and the retention structure and occlusive element can be sized to anchor within the canaliculus while in a second large profile configuration.

As shown in FIG. 4B, retention structure 430 and occlusive element 440 are in a large profile configuration. Such a large profile configuration can occur when the occlusive element and retention structure are placed in the canaliculus. In the large profile configuration, the length of occlusive element 440 and retention structure 430 is shorter than in the small profile configuration by a distance 450. The proximal end of retention structure 430 and occlusive element 440 can slide over sheath body 420 when the sheath body and retention structure assume the large profile configuration such that the proximal end of drug core 410 and sheath body 420 extend from the retention structure and occlusive element. In some embodiments, the sheath body is shorter than drug core 410 by distance 450 so that more of the drug core is exposed while the retention structure and occlusive element are in the large profile configuration than is exposed while the retention structure and occlusive element are in the small profile configuration. In such embodiments, the retention structure and occlusive element retract to expose the drug core.

Figure 5A:
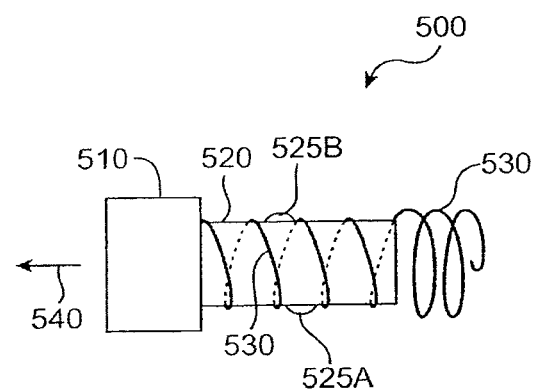
FIGS. 5A to 5C schematically illustrate replacement of a drug core and a sheath body, according to an embodiment of the present invention.

FIGS. 5A to 6 show embodiments of tools that can be used to insert many of the implants as describe herein.

FIG. 5A shows an insertion tool 500 to insert an implant into the punctum with a plunger 530 that can be depressed, according to an embodiment of the present invention. Insertion tool 500 includes a dilator 510 that can be inserted into the punctum to pre-dilate the punctum prior to insertion of an implant. An implant 520 can be pre-loaded onto tool 500 prior to dilation of the punctum. An internal wire 540 can be connected to implant 520 to retain the implant. Following pre-dilation of the punctum with dilator 510, tool 500 can be used to insert implant 520 into the punctum. While implant 520 is positioned in the punctum, plunger 530 can be depressed to engage wire 540 and release implant 520 from tool 500.

Figure 5B:
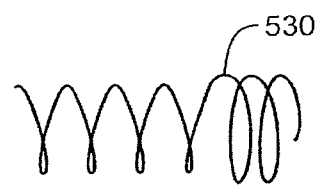

FIG. 5B shows an insertion tool 550 to insert an implant 570 into the punctum with a plunger that can slide, according to an embodiment of the present invention. Insertion tool 550 includes a dilator 560 with a conical section to dilate the punctum. Implant 550 includes a plunger 580 that can slide distally to advance implant 570 into the lumen. A shaft 590 is connected to plunger 580 to advance implant 570 distally when plunger 580 is advanced distally. While the punctum is dilated with dilator 560, plunger 580 can be advanced distally to place implant 570 in the canalicular lumen near the punctum. In many embodiments, a button can be depressed to advance distally the implant into the lumen, for example a button connected to shaft 590 with an intermediate mechanism.

FIG. 6 shows an insertion tool 600 to insert an implant into the punctum with a sheath 610 that retracts to position the implant in the canalicular lumen, according to an embodiment of the present invention. At least a portion of sheath 610 is shaped to dilate the punctum. Sheath 610 is shaped to hold an implant 620 in a small profile configuration. Insertion tool 600 includes an annular structure 615, which can comprise a portion of a body 605 of insertion tool 600. Sheath 610 and annular structure 615 are shaped to dilate the punctum and often comprise proximally inclined surfaces to dilate the punctum. Implant 620, sheath 610 and annular structure 615 can be at least partially inserted into the punctum to place the implant in the canalicular lumen. Annular structure 615 is disposed over sheath 610 so that sheath 610 can be retracted and slide under annular structure 615. A stop 625 can be connected to body 605 to retain implant 620 at the desired depth within the canalicular lumen while sheath 610 is retracted proximally to expose implant 620.

Once implant 620 has been positioned in the canalicular lumen at the desired depth in relation to the punctum, sheath 610 is retracted to expose implant 620 at the desired location in the canalicular lumen. A plunger 630 can be used to retract sheath 610. A shaft 640 mechanically couples sheath 610 to plunger 630. Thus, retraction of plunger 630 in the proximal direction can retract sheath 610 in the proximal direction to expose implant 620 at the desired location in the canalicular lumen. Implant 620 can be any of the implants as described herein. Often, implant 620 will comprise a resilient member that expands to a large profile configuration when sheath 610 is retracted. In many embodiments, insertion tool 600 can include a dilator to dilate the punctum prior to insertion of the implant, and the dilator can be positioned on an end of the insertion tool that opposes the end loaded with the implant, as described herein above.

Figure 5C:
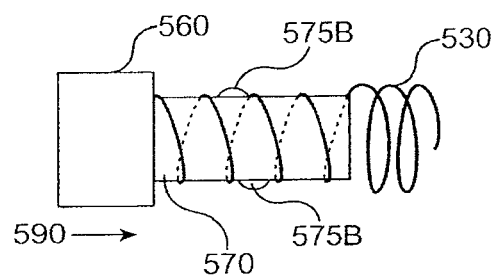

FIGS. 5A to 5C schematically illustrate replacement of a drug core 510 and a sheath body 520, according to an embodiment of the present invention. An implant 700 comprises drug core 510, sheath body 520 and a retention structure 530. Implant 500 can include an occlusive element support by and movable with retention structure 530. Often retention structure 530 can assume a first small profile configuration prior to implantation and a second large profile configuration while implanted. Retention structure 530 is shown in the large profile configuration and implanted in the canalicular lumen. Sheath body 520 includes extension 525A and extension 525B to attach the sheath body and drug core to retention structure 530 so that the sheath body and drug core are retained by retention structure 530. Drug core 510 and sheath body 520 can be removed together by drawing drug core 510 proximally as shown by arrow 530. Retention structure 530 can remain implanted in the canalicular tissue after drug core 510 and sheath body 520 have been removed as shown in FIG. 5B. A replacement core 560 and replacement sheath body 570 can be inserted together as shown in FIG. 5C. Such replacement can be desirable after drug core 510 has released effective amounts of therapeutic agent such that the supply of therapeutic agent in the drug core has diminished and the rate of therapeutic agent released is near the minimum effective level. Replacement sheath body 570 includes extension 575A and extension 575B. Replacement drug core 560 and replacement sheath body 570 can be advanced distally as shown by arrow 590 to insert replacement drug core 560 and replacement sheath body 570 into retention structure 530. Retention structure 530 remains at substantially the same location while replacement drug core 560 and replacement sheath body 570 are inserted into resilient member 530.

Figure 6A:
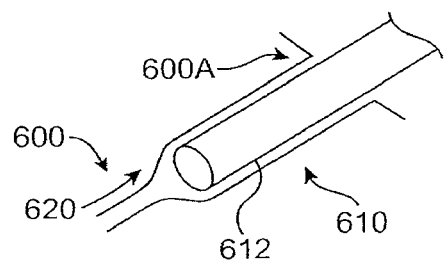
FIGS. 6A to 6C show deployment of a sustained release implant, according to an embodiment of the present invention.
Figure 6B:
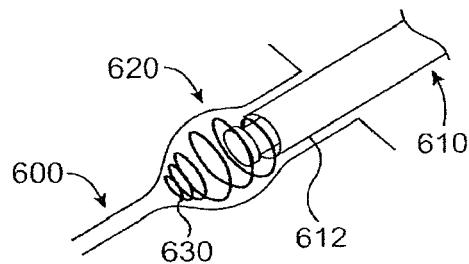
Figure 6C:
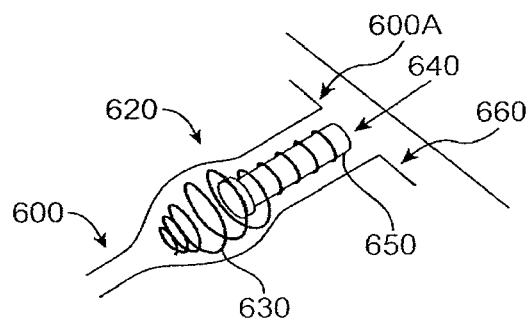

FIGS. 6A to 6C show deployment of a sustained release implant, according to an embodiment of the present invention. As shown in FIG. 6A, a deployment instrument 610 is inserted into a canaliculus 600 through a punctum 600A. A sustained release implant 620 is loaded into a tip of deployment instrument 610, and a sheath 612 covers sustained release implant 620. Retention structure 630 assumes a small profile configuration while sheath 612 is positioned over retention structure 630. As shown in FIG. 6B, outer sheath 612 of deployment instrument 610 is withdrawn to expose a retention structure 630 of sustained release implant 620. The exposed portion of retention element 630 assumes a large profile configuration. As shown in FIG. 6C, deployment instrument 610 has been removed and sustained release implant 620 is implanted in canaliculus 600. A drug core 640 is attached retention structure 630 and retained in the canaliculus. An outer body sheath 650 covers at least a portion of drug core 640 and drug core 640 releases a therapeutic agent into a liquid tear or tear film 660 near punctum 600A of canaliculus 600.

Sheath Body

The sheath body comprises appropriate shapes and materials to control migration of the therapeutic agent from the drug core. The sheath body houses the core and can fit snugly against the core. The sheath body is made from a material that is substantially impermeable to the therapeutic agent so that the rate of migration of the therapeutic agent may be largely controlled by the exposed surface area of the drug core that is not covered by the sheath body. In many embodiments, migration of the therapeutic agent through the sheath body can be about one tenth of the migration of the therapeutic agent through the exposed surface of the drug core, or less, often being one hundredth or less. In other words, the migration of the therapeutic agent through the sheath body is at least about an order of magnitude less that the migration of the therapeutic agent through the exposed surface of the drug core. Suitable sheath body materials include polyimide, polyethylene terephthalate" (hereinafter "PET"). The sheath body has a thickness, as defined from the sheath surface adjacent the core to the opposing sheath surface away from the core, from about 0.00025" to about 0.0015". The total diameter of the sheath that extends across the core ranges from about 0.2 mm to about 1.2 mm. The core may be formed by dip coating the core in the sheath material. Alternatively or in combination, the sheath body can comprise a tube and the core introduced into the sheath, for example as a liquid or solid that can be slid, injected and/or extruded into the sheath body tube. The sheath body can also be dip coated around the core, for example dip coated around a pre-formed core.

The sheath body can be provided with additional features to facilitate clinical use of the implant. For example, the sheath may receive a drug core that is exchangeable while the retention structure and sheath body remain implanted in the patient. The sheath body is often rigidly attached to the retention structure as described above, and the core is exchangeable while the retention structure retains the sheath body. In specific embodiments, the sheath body can be provided with external protrusions that apply force to the sheath body when squeezed and eject the core from the sheath body. Another drug core can then be positioned in the sheath body. In many embodiments, the sheath body and/or retention structure may have a distinguishing feature, for example a distinguishing color, to show placement such that the placement of the sheath body and/or retention structure in the canaliculus or other body tissue structure can be readily detected by the patient. The retention element and/or sheath body may comprise at least one mark to indicate the depth of placement in the canaliculus such that the retention element and/or sheath body can be positioned to a desired depth in the canaliculus based on the at least one mark.

Retention Structure

The retention structure comprises an appropriate material that is sized and shaped so that the implant can be easily positioned in the desired tissue location, for example the canaliculus. The retention structure is mechanically deployable and typically expands to a desired cross sectional shape, for example with the retention structure comprising a super elastic shape memory alloy such as NITANOL®. Other materials in addition to NITANOL® can be used, for example resilient metals or polymers, plastically deformable metals or polymers, shape memory polymers, and the like, to provide the desired expansion. In some embodiments polymers and coated fibers available from Biogeneral, Inc. of San Diego, Calif. may be used. Many metals such as stainless steels and non-shape memory alloys can be used and provide the desired expansion. This expansion capability permits the implant to fit in hollow tissue structures of varying sizes, for example canaliculae ranging from 0.3 mm to 1.2 mm (i.e. one size fits all).

Although a single retention structure can be made to fit canaliculae from 0.3 to 1.2 mm across, a plurality of alternatively selectable retention structures can be used to fit this range if desired, for example a first retention structure for canaliculae from 0.3 to about 0.9 mm and a second retention structure for canaliculae from about 0.9 to 1.2 mm The retention structure has a length appropriate to the anatomical structure to which the retention structure attaches, for example a length of about 3 mm for a retention structure positioned near the punctum of the canaliculus. For different anatomical structures, the length can be appropriate to provide adequate retention force, e.g. 1 mm to 15 mm lengths as appropriate.

Although the sheath body and drug core are attached to one end of the retention structure as described above, in many embodiments the other end of retention structure is not attached to drug core and sheath body so that the retention structure can slide over the sheath body and drug core while the retention structure expands. This sliding capability on one end is desirable as the retention structure may shrink in length as the retention structure expands in width to assume the desired cross sectional width. However, it should be noted that many embodiments may employ a sheath body that does not slide in relative to the core.

In many embodiments, the retention structure can be retrieved from tissue. A protrusion, for example a hook, a loop, or a ring, can extend from the retention structure to facilitate removal of the retention structure.

Occlusive Element

The occlusive element comprises an appropriate material that is sized and shaped so that the implant can at least partially inhibit, even block, the flow of fluid through the hollow tissue structure, for example lacrimal fluid through the canaliculus. The occlusive material shown is a thin walled membrane of a biocompatible material, for example silicone, that can expand and contract with the retention structure. The occlusive element is formed as a separate thin tube of material that is slid over the end of the retention structure and anchored to one end of the retention structure as described above. Alternatively, the occlusive element can be formed by dip coating the retention structure in a biocompatible polymer, for example silicone polymer. The thickness of the occlusive element can be in a range from about 0.01 mm to about 0.15 mm, and often from about 0.05 mm to 0.1 mm.

Therapeutic Agents

A "therapeutic agent" can comprise a drug may be any of the following or their equivalents, derivatives or analogs, including, anti-glaucoma medications, (e.g. adrenergic agonists, adrenergic antagonists (beta blockers), carbonic anhydrase inhibitors (CAIS, systemic and topical), parasympathomimetics, prostaglandins and hypotensive lipids, and combinations thereof), antimicrobial agent (e.g., antibiotic, antiviral, antiparacytic, antifungal, etc.), a coiticosteroid or other anti-inflammatory (e.g., an NSAID), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic or the like. Examples of conditions that may be treated with the therapeutic agent(s) include but are not limited to glaucoma, pre and post surgical treatments, dry eye and allergies. In some embodiments, the therapeutic agent may be a lubricant or a surfactant, for example a lubricant to treat dry eye.

Exemplary therapeutic agents include, but are not limited to, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Such anti inflammatory steroids contemplated for use in the methodology of the present invention, include triamcinolone acetonide (generic name) and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fluorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, pholine iodine, demecarium bromide); antineoplastics (such as carmustine, cisplatin, fluorouracil3; immunological drugs (such as vaccines and immune stimulants); hormonal agents (such as estrogens, —estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as Bimatoprost, travoprost, Latanoprost etc; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

The amount of drug associated with the drug-delivery device may vary depending on the particular agent, the desired therapeutic benefit and the time during which the device is intended to deliver the therapy. Since the devices of the present invention present a variety of shapes, sizes and delivery mechanisms, the amount of drug associated with the device will depend on the particular disease or condition to be treated, and the dosage and duration that is desired to achieve the therapeutic effect. Generally, the amount of drug is at least the amount of drug that upon release from the device, is effective to achieve the desired physiological or pharmacological local or systemic effects.

Embodiments of the drug delivery devices of the present invention can be adapted to provide delivery of drug at a daily rate that is substantially below the therapeutically effective drop form of treatment so as to provide a large therapeutic range with a wide safety margin. For example, many embodiments treat the eye with therapeutic levels for extended periods that are no more than 5 or 10 percent of the daily drop dosage. Consequently, during an initial bolus or washout period of about one to three days, the implant can elute the therapeutic agent at a rate that is substantially higher than the sustained release levels and well below the daily drop form dosage. For example, with an average sustained release level of 100 ng per day, and an initial release rate of 1000 to 1500 ng per day, the amount of drug initially released is less than the 2500 ng of drug that may be present in a drop of drug delivered to the eye. This used use of sustained release levels substantially below the amount of drug in a drop and/or drops administered daily allows the device to release a therapeutically beneficial amount of drug to achieve the desired therapeutic benefit with a wide safety margin, while avoiding an inadequate or excessive amount of drug at the intended site or region.

An extended period of time may mean a relatively short period of time, for example minutes or hours (such as with the use of an anesthetic), through days or weeks (such as the use of pre-surgical or post-surgical antibiotics, steroids, or NSAIDs and the like), or longer (such as in the case of glaucoma treatments), for example months or years (on a recurring basis of use of the device).

For example, a drug such as Timolol maleate, a beta1 and beta2 (non-selective) adrenergic receptor blocking agent can be used in the device for a release over an extended period of time such as 3 months. Three months is a relatively typical elapsed time between physician visits for a glaucoma patient undergoing topical drop therapy with a glaucoma drug, although the device could provide treatment for longer or shorter durations. In the three month example, a 0.25% concentration of Timolol translates to from 2.5 to 5 mg/1000 µL, typically being 2.5 mg/1 000 µL A drop of Timolol for topical application is usually in the range of 40-60 µL, typically being 50 µL. Thus, there may be 0.08-0.15 mg, typically being 0.125 mg of Timolol in a drop. There may be approximately 8% (optionally 6-10%) of the drop left in the eye after 5 minutes, so about 10 .mu·g of the drug is available at that time. Timolol may have a bioavailability of 30-50%, which means that from 1.5 to 7.5 µg, for example 4 µg of the drug is available to the eye. Timolol is generally applied twice a day, so 8 (or 3-15) µg is available to the eye each day. Therefore, a delivery device might contain from 270 to 1350 for example 720 µg, of the drug for a 90 day, or 3 month, extended release. The drug would be contained within the device and eluted based on the polymer or drug/hydrogel concentration. The drug can be similarly contained on the device and eluted for olopatadine hydrochloride (PATANOL®) and other drugs in a manner similar to Timolol.

Commercially available solutions of Timolol maleate are available in 0.25% and 0.5% preparations, and the initial dosage can be 1 drop twice per day of 0.25% solution. A 0.25% concentration of Timolol is equivalent to 2.5 mg per 1000 µl. A sustained release quantity of Timolol released each day from the drug core can be from about 3 to 15 µg each day. Although the sustained release quantity delivered each day from the device may vary, a sustained release delivery of about 8 μg per day corresponds to about 3.2% of the 0.250 mg of Timolol applied with two drops of a 0.25% solution.

For example, in the case of Latanoprost (Xalatan), a prostaglandin F2α analogue, this glaucoma medication has concentrations that are about $1/10^{th}$ that of Timolol. Therefore, the amount of drug on the implantable device, depending on the bioavailability, would be significantly less—approximately 20-135 μg and typically 50-100 μg—for Latanoprost and other prostaglandin analogues. This also translates to a device that can either be smaller than one required for a beta blocker delivery or can house more drug for a longer release period.

A drop of Xalatan contains about 2.5 μg of Latanoprost, assuming a 50 μL drop volume. Therefore, assuming that about 8% of 2.5 μg is present 5 minutes after instillation, only about 200 ng of drug remains on the eye. Based on the Latanoprost clinical trials, this amount is effective in lowering IOP for at least 24 hours. Pfizer/Pharmacia conducted several dose-response studies in support of the NDA for Xalatan. The doses ranged from 12.5 μg/mL to 115 μ/mL of Latanoprost. The current dose of Latanoprost, 50 μg/mL, given once per day, was shown to be optimal. However, even the lowest doses of 12.5 μg/mL QD or 15 μg/mL BID consistently gave about 60-75% of the IOP reduction of the 50 μg/mL QD dose. Based on the assumptions above, a 12.5 μg/mL concentration provides 0.625 μg of Latanoprost in a 50 μL drop, which results in only about 50 ng (8%) of drug remaining in the eye after 5 minutes.

In many embodiments, the concentrations of Latanoprost are about $1/100^{th}$, or 1 percent, that of Timolol, and in specific embodiments the concentrations of Latanoprost may be about $1/50^{th}$, or 2 percent, that of Timolol. For example, commercially available solution preparations of Latanoprost are available at concentrations 0.005%, often delivered with one drop per day. In many embodiments, the therapeutically effective concentration of drug released from the device per day can be about $1/100^{th}$ of Timolol, about 30 to 150 ng per day, for example about 80 ng, assuming tear washout and bioavailability similar to Timolol. For example, the amount of drug on the implantable device, can be significantly less—approximately 1% to 2% of Timolol, for example 2.7 to 13.5 μg, and can also be about 3 to 20 μg, for Latanoprost and other prostaglandin analogues. Although the sustained release amount of Latanoprost released each day can vary, a sustained release of 80 ng per day corresponds to about 3.2% of the 2.5 μg of Latanoprost applied with a single drop of a 0.005% solution.

For example, in the case of Bimatoprost (Lumigan), a synthetic prostamide prostaglandin analogue, this glaucoma medication may have concentrations that are $1/20^{th}$ or less than that of Timolol. Therefore, the amount of drug loaded on the extended release device for a 3 to 6 month extended release, depending on the bioavailability, can be significantly less, approximately 5-30 μg and typically 10-20 μg—for Bimatoprost and analogues and derivatives thereof. In many embodiments, the implant can house more drug for a longer sustained release period, for example 20-40 μg for a sustained release period of 6 to 12 months with Bimatoprost and its derivatives. This decrease in drug concentration can also translate to a device that can be smaller than one required for a beta blocker delivery.

Commercially available solution concentrations of Bimatoprost are 0.03% by weight, often delivered once per day. Although the sustained release amount of Bimatoprost released each day can vary, a sustained release of 300 ng per day corresponds to about 2% of the 15 μg of Bimatoprost applied with a single drop of a 0.03% solution. Work in relation with the present invention suggests that even lower sustained release doses of Bimatoprost can provide at least some reduction in intraocular pressure, for example 20 to 200 ng of Bimatoprost and daily sustained release dosages of 0.2 to 2% of the daily drop dosage.

For example, in the case of Travoprost (Travatan), a prostaglandin F2.alpha. analogue, this glaucoma medication may have concentrations that are 2% or less than that of Timolol. For example, commercially available solution concentrations are 0.004%, often delivered once per day. In many embodiments, the therapeutically effective concentration of drug released from the device per day can be about 65 ng, assuming tear washout and bioavailability similar to Timolol. Therefore, the amount of drug on the implantable device, depending on the bioavailability, would be significantly less. This also translates to a device that can either be smaller than one required for a beta blocker delivery or can house more drug for a longer release period. For example, the amount of drug on the implantable device, can be significantly less—approximately $1/100$ of Timolol, for example 2.7 to 13.5 μg, and typically about 3 to 20 μg, for Travoprost, Latanoprost and other prostaglandin F2α analogues. Although the sustained release amount of Latanoprost released each day can vary, a sustained release of 65 ng per day corresponds to about 3.2% of the 2.0 μg of Travoprost applied with a single drop of a 0.004% solution.

In some embodiments, the therapeutic agent may comprise a cortico steroid, for example fluocinolone acetonide, to treat a target ocular tissue. In specific embodiments, fluocinolone acetonide can be released from the canaliculus and delivered to the retina as a treatment for diabetic macular edema (DME).

It is also within the scope of this invention to modify or adapt the devices to deliver a high release rate, a low release rate, a bolus release, a burst release, or combinations thereof. A bolus of the drug may be released by the formation of an erodable polymer cap that is immediately dissolved in the tear or tear film. As the polymer cap comes in contact with the tear or tear film, the solubility properties of the polymer enable the cap to erode and the drug is released all at once. A burst release of a drug can be performed using a polymer that also erodes in the tear or tear film based on the polymer solubility. In this example, the drug and polymer may be stratified along the length of the device so that as the outer polymer layer dissolves, the drug is immediately released. A high or low release rate of the drug could be accomplished by changing the solubility of the erodable polymer layer so that the drug layer released quickly or slowly. Other methods to release the drug could be achieved through porous membranes, soluble gels (such as those in typical ophthalmic solutions), microparticle encapsulations of the drug, or nanoparticle encapsulation, depending on the size of the drug molecule.

Drug Core

The drug core comprises the therapeutic agent and materials to provide sustained release of the therapeutic agent. The therapeutic agent migrates from the drug core to the target tissue, for example ciliary muscles of the eye. The therapeutic agent may optionally be only slightly soluble in the matrix so that a small amount of therapeutic agent is dissolved in the matrix and available for release from the surface of drug core 110. As the therapeutic agent diffuses from the exposed surface of the core to the tear or tear film, the rate of migration from the core to the tear or tear film can be related to the concentration of therapeutic agent dissolved in the matrix. In addition or in combination, the rate of migration of therapeutic agent from the core to the tear or tear film can be related to properties of the matrix in which the therapeutic agent dissolves. In specific embodiments, the rate of migration from the drug core to the tear or tear film can be based on a silicone formulation. In some embodiments, the concentration of therapeutic agent dissolved in the drug core may be controlled to provide the desired rate of release of the therapeutic agent. The therapeutic agent included in the core can include liquid, solid, solid gel, solid crystalline, solid amorphous, solid particulate, and/or dissolved forms of the therapeutic agent. In a preferred embodiment, the drug core comprises a silicone matrix containing the therapeutic agent. The therapeutic agent may comprise liquid or solid inclusions, for example liquid Latanoprost droplets or solid Bimatoprost particles, respectively, dispersed in the silicone matrix.

The drug core can comprise one or more biocompatible materials capable of providing a sustained release of the therapeutic agent. Although the drug core is described above with respect to an embodiment comprising a matrix with a substantially non-biodegradable silicone matrix with inclusions of the drug located therein that dissolve, the drug core can include structures that provide sustained release of the therapeutic agent, for example a biodegradable matrix, a porous drug core, liquid drug cores and solid drug cores. A matrix that contains the therapeutic agent can be formed from either biodegradable or non-biodegradable polymers. A non-biodegradable drug core can include silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., NITANOL®), titanium, stainless steel, cobalt-chrome alloy (e.g., ELGILOY® from Elgin Specialty Metals, Elgin, Ill.; CONICHROME® from Carpenter Metals Corp., Wyomissing, Pa.). A biodegradable drug core can comprise one or more biodegradable polymers, such as protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some embodiments the drug core can comprise at least one of hydrogel polymer.

Release of Therapeutic Agent at Effective Levels

The rate of release of the therapeutic agent can be related to the concentration of therapeutic agent dissolved in the drug core. In many embodiments, the drug core comprises non-therapeutic agents that are selected to provide a desired solubility of the therapeutic agent in the drug core. The non-therapeutic agent of the drug core can comprise polymers as described herein and additives. A polymer of the core can be selected to provide the desired solubility of the therapeutic agent in the matrix. For example, the core can comprise hydrogel that may promote solubility of hydrophilic treatment agent. In some embodiments, functional groups can be added to the polymer to provide the desired solubility of the therapeutic agent in the matrix. For example, functional groups can be attached to silicone polymer.

In some embodiments, additives may be used to control the release kinetics of therapeutic agent. For example, the additives may be used to control the concentration of therapeutic agent by increasing or decreasing solubility of the therapeutic agent in the drug core so as to control the release kinetics of the therapeutic agent. The solubility may be controlled by providing appropriate molecules and/or substances that increase and/or decrease the solubility of the dissolved from of the therapeutic agent to the matrix. The solubility of the dissolved from the therapeutic agent may be related to the hydrophobic and/or hydrophilic properties of the matrix and therapeutic agent. For example, surfactants, tinuvin, salts and water can be added to the matrix and may increase the solubility of hydrophilic therapeutic agent in the matrix. In addition, oils and hydrophobic molecules and can be added to the matrix and may increase the solubility of hydrophobic treatment agent in the matrix.

Instead of or in addition to controlling the rate of migration based on the concentration of therapeutic agent dissolved in the matrix, the surface area of the drug core can also be controlled to attain the desired rate of drug migration from the core to the target site. For example, a larger exposed surface area of the core will increase the rate of migration of the treatment agent from the drug core to the target site, and a smaller exposed surface area of the drug core will decrease the rate of migration of the therapeutic agent from the drug core to the target site. The exposed surface area of the drug core can be increased in any number of ways, for example by any of castellation of the exposed surface, a porous surface having exposed channels connected with the tear or tear film, indentation of the exposed surface, protrusion of the exposed surface. The exposed surface can be made porous by the addition of salts that dissolve and leave a porous cavity once the salt dissolves. Hydrogels may also be used, and can swell in size to provide a larger exposed surface area. Such hydrogels can also be made porous to further increase the rate of migration of the therapeutic agent.

Further, an implant may be used that includes the ability to release two or more drugs in combination, such as the structure disclosed in U.S. Pat. No. 4,281,654 (Shell). For example, in the case of glaucoma treatment, it may be desirable to treat a patient with multiple prostaglandins or a prostaglandin and a cholinergic agent or an adrenergic antagonist (beta blocker), such as ALPHAGAN®, or a prostaglandin and a carbonic anhydrase inhibitor.

In addition, drug impregnated meshes may be used such as those disclosed in US Patent Publication No. 2002/0055701 or layering of biostable polymers as described in US Patent Publication No. 2005/0129731. Certain polymer processes may be used to incorporate drug into the devices of the present invention such as, so-called "self-delivering drugs" or PolymerDrugs (Polymerix Corporation, Piscataway, N.J.) are designed to degrade only into therapeutically useful compounds and physiologically inert linker molecules, further detailed in US Patent Publication No. 2005/0048121 (East), hereby incorporated by reference in its entirety. Such delivery polymers may be employed in the devices of the present invention to provide a release rate that is equal to the rate of polymer erosion and degradation and is constant throughout the course of therapy. Such delivery polymers may be used as device coatings or in the form of microspheres for a drug depot injectable (such as a reservoir of the present invention). A further polymer delivery technology may also be adapted to the devices of the present invention such as that described in US Patent Publication No. 2004/0170685 (Carpenter), and technologies available from Medivas (San Diego, Calif.).

In specific embodiments, the drug core matrix comprises a solid material, for example silicone, that encapsulates inclusions of the drug. The drug comprises molecules which are very insoluble in water and slightly soluble in the encapsulating drug core matrix. The inclusions encapsulated by the drug core can be micro-particles having dimensions from about 1 μm to about 100 μm across. The drug inclusions can comprise crystals, for example Bimatoprost crystals, and/or droplets of oil, for example with Latanoprost oil. The drug inclusions can dissolve into the solid drug core matrix and substantially saturate the drug core matrix with the drug, for example dissolution of Latanoprost oil into the solid drug core matrix. The drug dissolved in the drug core matrix is transported, often by diffusion, from the exposed surface of the drug core into the tear film. As the drug core is substantially saturated with the drug, in many embodiments the rate limiting step of drug delivery is transport of the drug from the surface of the drug core matrix exposed to the tear film. As the drug core matrix is substantially saturated with the drug, gradients in drug concentration within the matrix are minimal and do not contribute significantly to the rate of drug delivery. As surface area of the drug core exposed to the tear film is nearly constant, the rate of drug transport from the drug core into the tear film can be substantially constant. Work in relation with the present invention suggests that the solubility of the therapeutic agent in water and molecular weight of the drug can effect transport of the drug from the solid matrix to the tear. In many embodiments, the therapeutic agent is nearly insoluble in water and has a solubility in water of about 0.03% to 0.002% by weight and a molecular weight from about 400 grams/mol. to about 1200 grams/mol.

In many embodiments the therapeutic agent has a very low solubility in water, for example from about 0.03% by weight to about 0.002% by weight, a molecular weight from about 400 grams per mole (g/mol.) to about 1200 g/mol, and is readily soluble in an organic solvent. Cyclosporin A (CsA) is a solid with an aqueous solubility of 27.67 µg/mL at 25° C., or about 0.0027% by weight, and a molecular weight (M.W.) of 1202.6 g/mol. Latanoprost (Xalatan) is a prostaglandin F2α analogue, a liquid oil at room temperature, and has an aqueous solubility of 50 µg/mL in water at 25° C., or about 0.005% by weight and a M.W. of 432.6 g/mol. Bimatoprost (Lumigan) is a synthetic prostamide analogue, a solid at room temperature solubility in water of 300 µg/mL in water at 25° C., or 0.03% by weight, and has a M.W. of 415.6 g/mol.

Work in relation with the present invention indicates that naturally occurring surfactants in the tear film, for example surfactant D and phospholipids, may effect transport of the drug dissolved in the solid matrix from the core to the tear film. The drug core can be adapted in response to the surfactant in the tear film to provide sustained delivery of the drug into the tear film at therapeutic levels. For example, empirical data can be generated from a patient population, for example 10 patients whose tears are collected and analyzed for surfactant content. Elution profiles in the collected tears for a drug that is sparingly soluble in water, for example cyclosporine, can also be measured and compared with elution profiles in buffer and surfactant such that an in vitro model of tear surfactant is developed. An in vitro solution with surfactant based on this empirical data can be used to adjust the drug core in response to the surfactant of the tear film.

The drug cores may also be modified to utilize carrier vehicles such as nanoparticles or microparticles depending on the size of the molecule to be delivered such as latent-reactive nanofiber compositions for composites and nanotextured surfaces (Innovative Surface Technologies, LLC, St. Paul, Minn.), nanostructured porous silicon, known as Bio-Silicont, including micron sized particles, membranes, woven fibers or micromachined implant devices (pSividia, Limited, UK) and protein nanocage systems that target selective cells to deliver a drug (Chimeracore).

In many embodiments, the drug insert comprises of a thin-walled polyimide tube sheath with a drug core comprising Latanoprost dispersed in Nusil 6385 (MAF 970), a medical grade solid silicone that serves as the matrix for drug delivery. The distal end of the drug insert is sealed with a cured film of solid Loctite 4305 medical grade adhesive. The drug insert may be placed within the bore of the punctum plug, the Loctite 4305 adhesive does not come into contact with either tissue or the tear film. The inner diameter of the drug insert can be 0.32 mm; and the length can be 0.95 mm. Three Latanoprost concentrations in the finished drug product can be tested clinically: Drug cores can comprise 3.5, 7 or 14 µg Latanoprost, with percent by weight concentrations of 5, 10 and 20% respectively. Assuming an overall elution rate of approximately 100 ng/day, the drug core comprising 14 µg of Latanoprost is adapted to deliver drug for approximately at least 100 days, for example 120 days. The overall weight of the drug core, including Latanoprost, can be ~70 µg. The weight of the drug insert including the polyimide sleeve can be approximately 100 µg.

In many embodiments, the drug core may elute with an initial elevated level of therapeutic agent followed by substantially constant elution of the therapeutic agent. In many instances, an amount of therapeutic agent released daily from the core may be below the therapeutic levels and still provide a benefit to the patient. An elevated level of eluted therapeutic agent can result in a residual amount of therapeutic agent and/or residual effect of the therapeutic agent that is combined with a sub-therapeutic amount of therapeutic agent to provide relief to the patient. In embodiments where therapeutic level is about 80 ng per day, the device may deliver about 100 ng per day for an initial delivery period. The extra 20 ng delivered per day can have a beneficial effect when therapeutic agent is released at levels below the therapeutic level, for example at 60 ng per day. As the amount of drug delivered can be precisely controlled, an initial elevated dose may not result in complications and/or adverse events to the patient.

Example 1

Latanoprost Drug Core Elution Data

Drug cores as described above have been fabricated with different cross sectional sizes of 0.006 inches, 0.012 inches, and 0.025 inches, and drug concentrations of 5%, 10% and 20% in a silicone matrix. Theses drug cores can be made with a Syringe Tube and Cartridge Assembly, Mixing Latanoprost with Silicone, and Injecting the mixture into a polyimide tube which is cut to desired lengths and sealed. The length of the drug cores were approximately 0.80 to 0.95 mm, which for a diameter of 0.012 inches (0.32 mm) corresponds to total Latanoprost content in the drug cores of approximately 3.5 µg, 7 µg and 14 µg for concentrations of 5%, 10% and 20%, respectively.

Syringe Tube and Cartridge Assembly. 1. Take polyimide tubing of three different diameters 0.006 inches, 0.0125 inches and 0.025 inches. 2. Cut polyimide tubing of different diameters to ~15 cm length. 3. Insert Polyimide tubes into a Syringe Adapter. 4. Adhesive bond polyimide tube into luer adapter (Loctite, low viscosity UV cure). 5. Trim end of assembly. 6. Clean the cartridge assembly using distilled water and then with methanol and dry it in oven at 60° C.

Mix Latanoprost with Silicone. Prepare Latanoprost. Latanoprost is provided as a 1% solution in methylacetate. Place the appropriate amount of solution into a dish and using a nitrogen stream, evaporate the solution until only the Latanoprost remains. Place the dish with the Latanoprost oil under vacuum for 30 minutes. Combine Latanoprost with silicone. Prepare three different concentrations of Latanoprost (5%, 10% and 20%) in silicon Nusil 6385 and inject it into tubing of different diameters (0.006 in, 0.012 in and 0.025 inches) to generate 3×3 matrixes. The percent of Latanoprost to silicone is determined by the total weight of the drug matrix. Calculation: Weight of Latanoprost/(weight of Latanoprost+weight of silicone)×100=percent drug.

Inject tube. 1. Insert Cartridge and Polyimide tubes assembly into 1 ml syringe. 2. Add one drop of catalyst, (MED-6385 Curing Agent) in the syringe. 3. Force excess catalyst out of the polyimide tube with clean air. 4. Fill syringe with silicone drug matrix. 5. Inject tube with drug matrix until the tube is filled or the syringe plunger becomes too difficult to push. 6. Close off the distal end of the polyimide tube and maintain pressure until the silicone begins to solidify. 7. Allow to cure at room temperature for 12 hours. 8. Place under vacuum for 30 minutes. 9. Place tube in right size trim fixture (prepared in house to hold different size tubing) and cut drug inserts to length (0.80-0.95 mm).

Testing. Elution study (in vitro). 1. Place 10 plugs of same size and same concentration per centrifuge tube and add 1.5 ml of 7.4 pH buffer solution to it. 2. Change the solvent with fresh 7.4 pH buffer after appropriate time. 3. Take HPLC of the elutant at 210 nm with PDA detector 2996 using Sunfire C18, 3 mm×10 mm column (Waters Corporation, Milford, Mass.). Acetonitrile and water mixture is used for gradient elution. Calibration was done in house before and after each analysis, using in-house standards with precisely weighed concentration of Latanoprost. 4. Calculate the amount of drug release per day per device for different size tubings having different concentrations of Latanoprost. 5. Plot elution rate vs area and concentration for day 1 and day 14.

Figure 7A:
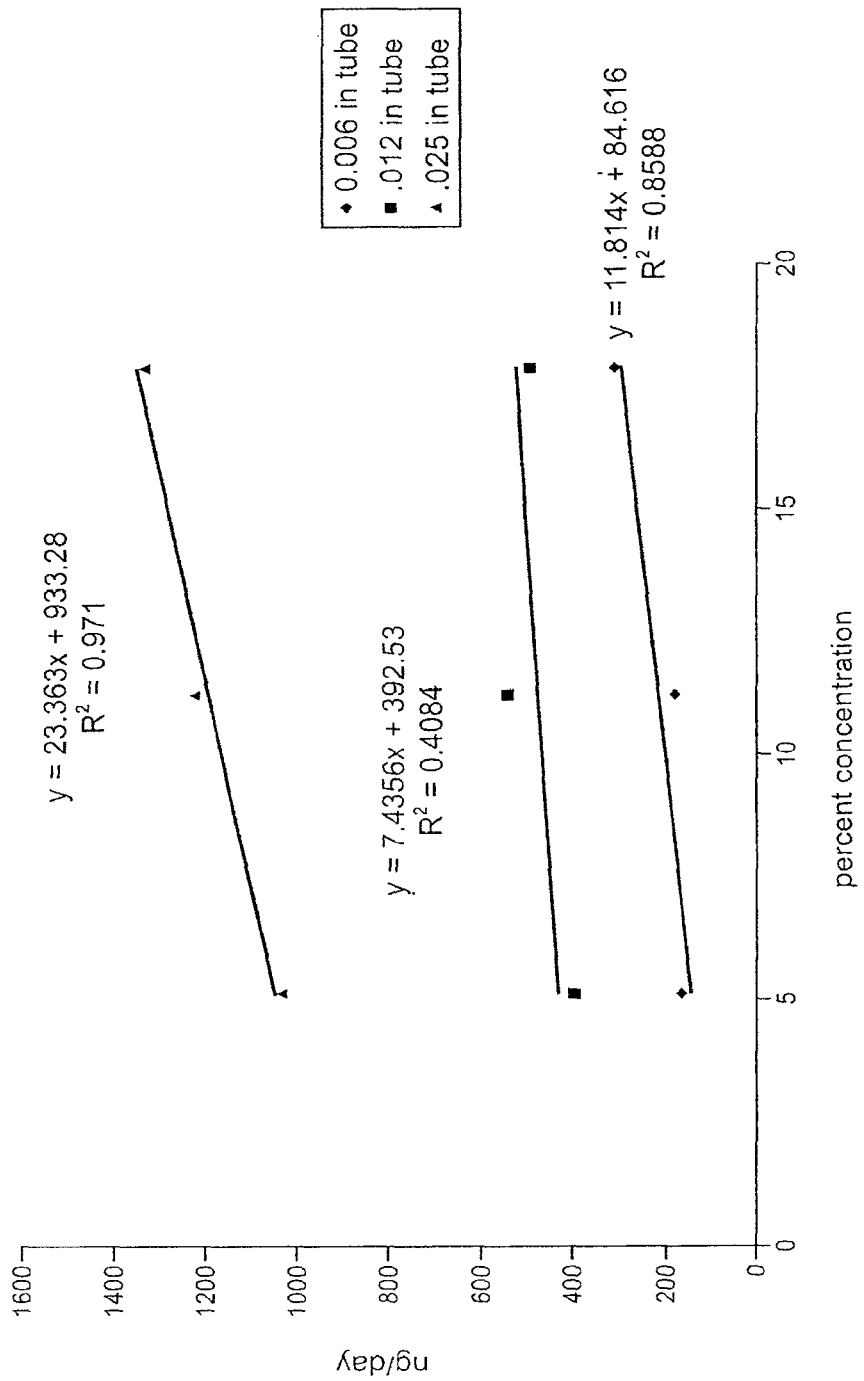
FIGS. 7A and 7B show elution data of Latanoprost at day 1 and day 14, respectively, for the three core diameters of 0.006, 0.012 and 0.025 inches and three Latanoprost concentrations of approximately 5%, 11% and 18%, according to embodiments of the present invention.
Figure 7B:
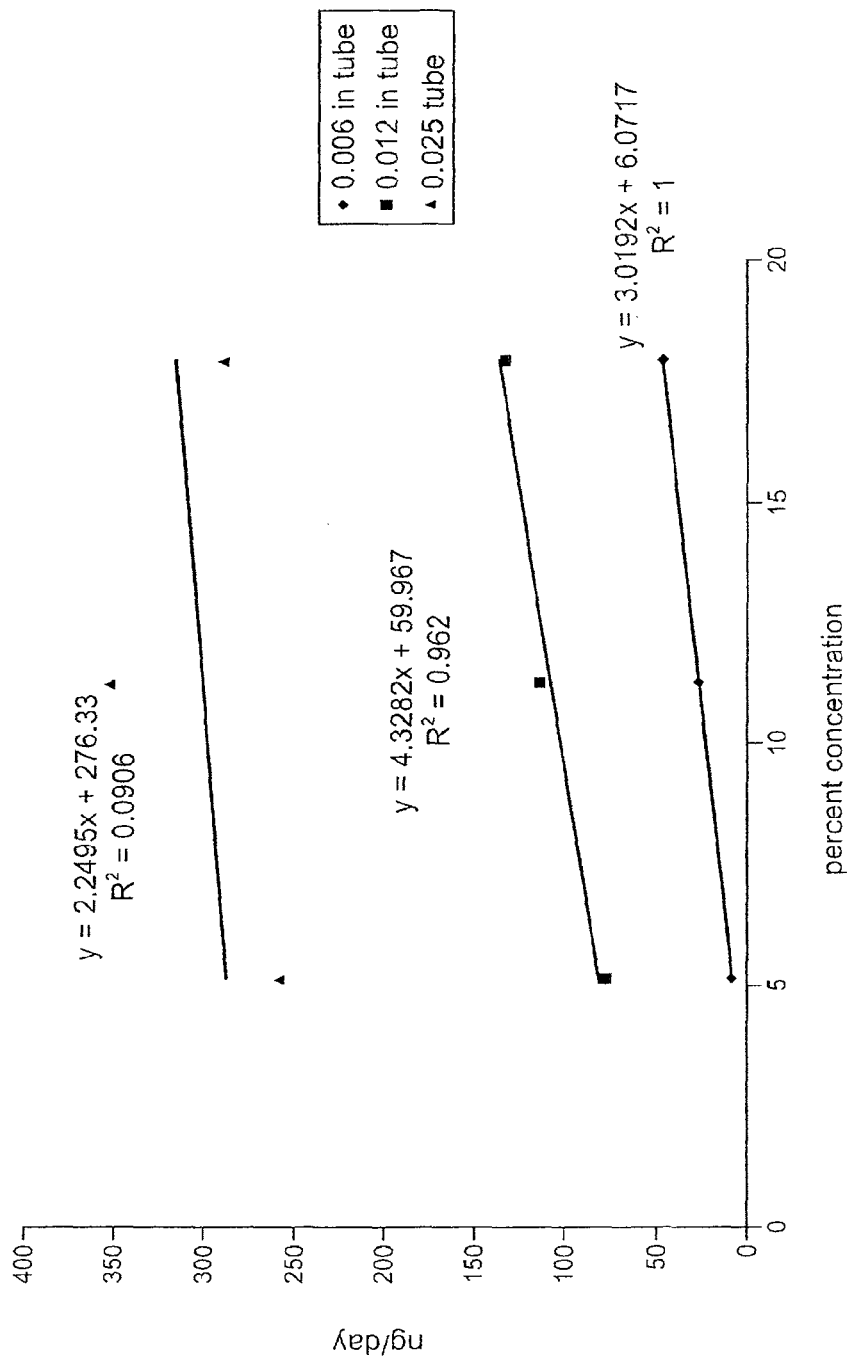

FIGS. 7A and 7B show elution data of Latanoprost at day 1 and day 14, respectively, for the three core diameters of 0.006, 0.012 and 0.025 inches and three Latanoprost concentrations of approximately 5%, 11% and 18%. Elution rate of the Latanoprost in nanograms (ng) per day is plotted versus percent concentration. These data show that the rate of elution is mildly dependent on the concentration and strongly dependent on the exposed surface area at both time periods. At day 1, the 0.006 inch, 0.012 inch and 0.025 inch diameter cores released about 200 ng, 400 ng and 1200 ng of Latanoprost, respectively, showing that the quantity of Latanoprost released increases with an increased size of the exposed surface area of the drug core. For each tube diameter, the quantity of Latanoprost released is compared to the concentration of drug in the drug core with a least square regression line. For the 0.006, 0.012 and 0.025 inch drug cores the slope of the regression lines are 11.8, 7.4 and 23.4, respectively. These values indicate that a doubling of concentration of the Latanoprost drug in the core does not lead to a doubling of the elution rate of the Latanoprost from the core, consistent with droplets of Latanoprost suspended in a drug core matrix and substantial saturation of the drug core matrix with Latanoprost dissolved therein, as described above.

At day 14, the 0.006 inch, 0.012 inch (0.32 mm) and 0.025 inch diameter cores released about 25 ng, 100 ng and 300 ng of Latanoprost, respectively, showing that the quantity of Latanoprost released increases with an increased size of the exposed surface area of the drug core at extended periods of time, and that the quantity of Latanoprost released is mildly dependent on the concentration of therapeutic agent in the core. For each tube diameter, the quantity of Latanoprost released is compared to the concentration of drug in the drug core with a least square regression line. For the 0.006, 0.012 and 0.025 inch drug cores the slope of the regression lines are 3.0, 4.3 and 2.2, respectively. For the 0.012 and 0.025 inch cores, these values indicate that a doubling of concentration of the Latanoprost drug in the core does not lead to a doubling of the elution rate of the Latanoprost from the core, consistent with droplets of Latanoprost suspended in a drug core matrix and substantial saturation of the drug core matrix with Latanoprost dissolved therein, as described above. However, for the 0.006 inch diameter core, there is an approximately first order relationship between the quantity of initially in the core and the amount of drug released at day 14, which can may be caused by depletion of Latanoprost drug droplets in the core.

Figure 7C:
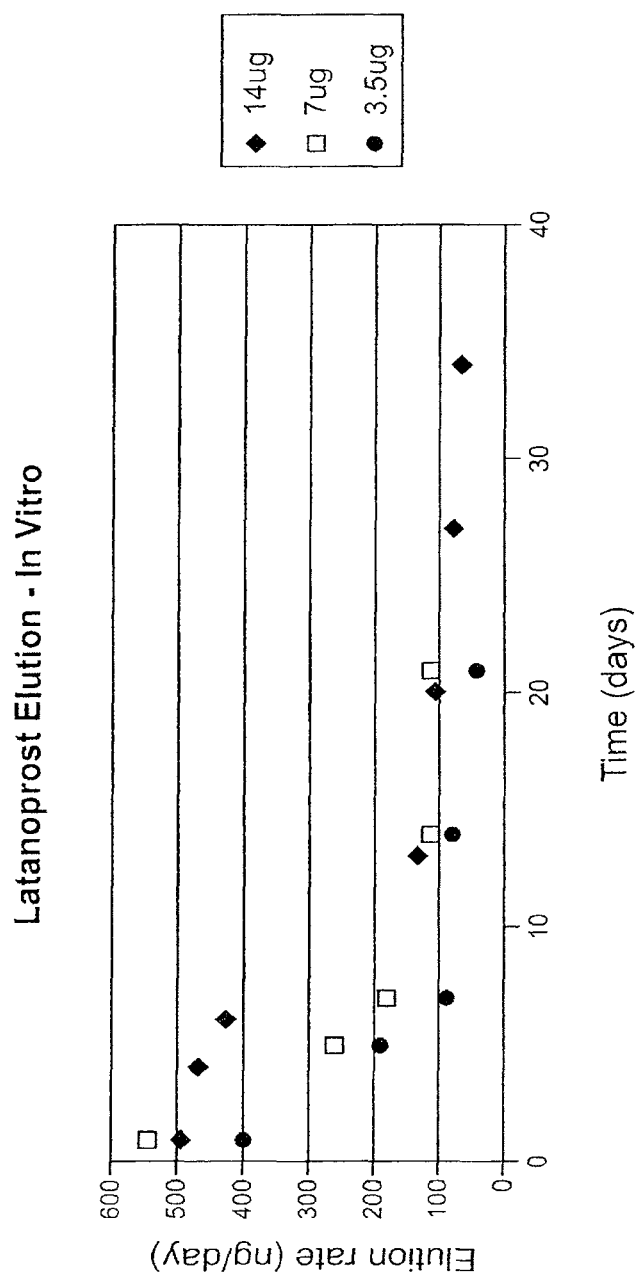
FIG. 7C shows elution data for Latanoprost from 0.32 mm diameter, 0.95 mm long drug cores with concentrations of 5, 10 and 20% and drug weights of 3.5, 7 and 14 ng, respectively, according to embodiments of the present invention.
Figure 7E:
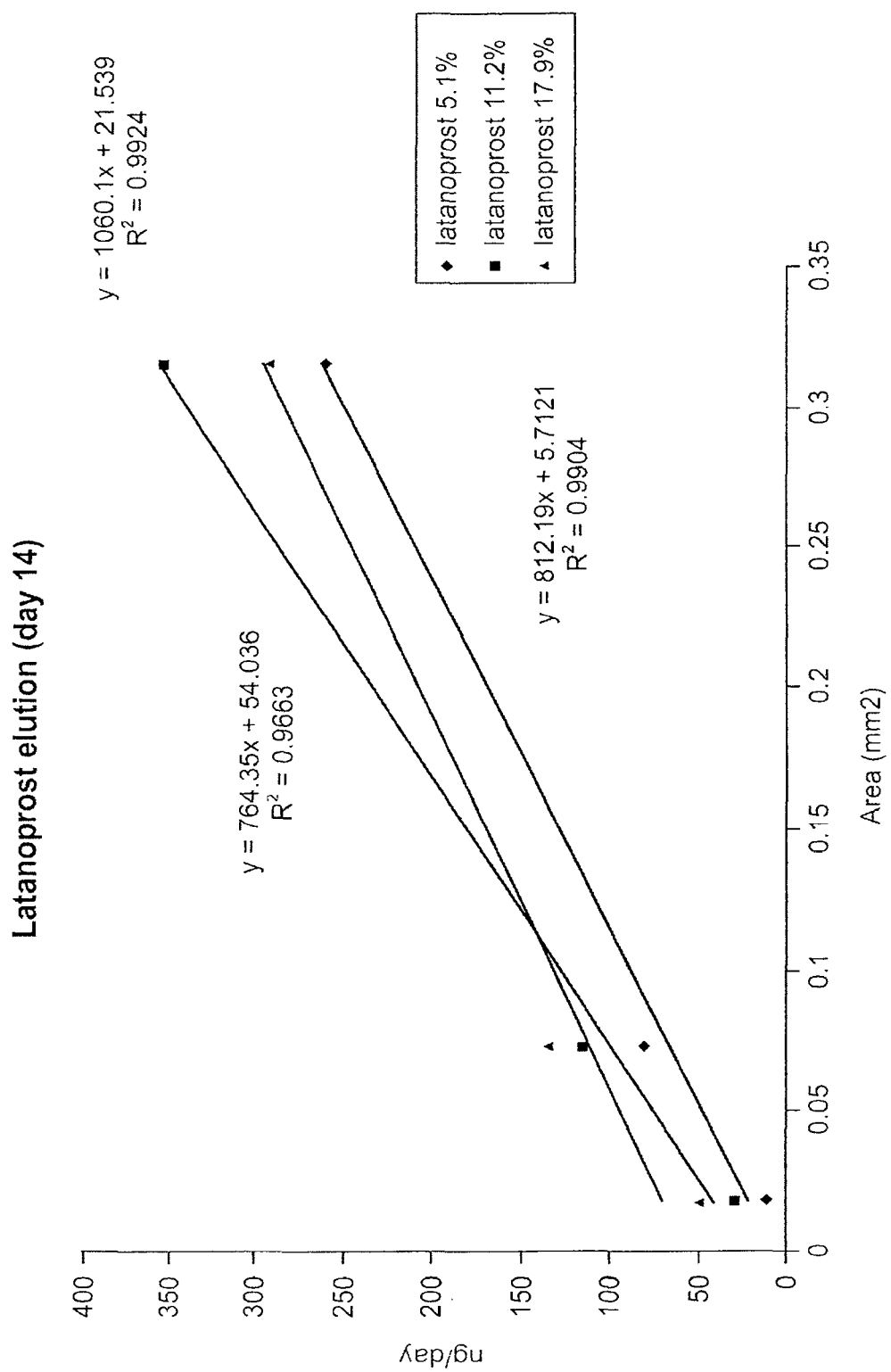

FIGS. 7D and 7E show dependence of the rate of elution on exposed surface area of the drug core for the three core diameters and the three concentrations as in FIGS. 7A and 7B Latanoprost at day 1 and day 14, respectively, according to embodiments of the present invention. Elution rate of the Latanoprost in nanograms (ng) per day is plotted versus the exposed surface area of the drug core in $mm^2$ as determined by the diameter of the drug core.

These data show that the rate of elution is mildly dependent on the concentration of drug in the core and strongly dependent on the exposed surface area at both one day and at 14 days. The exposed surface areas of the 0.006 inch, 0.012 inch and 0.025 inch diameter cores are approximately 0.02, 0.07, and 0.32 $mm^2$, respectively. At day 1, the 0.02, 0.07, and 0.32 $mm^2$, cores released about 200 ng, 400 ng and 1200 ng of Latanoprost, respectively, showing that the quantity of Latanoprost released increases with an increased size of the exposed surface area of the drug core. For each concentration of therapeutic agent in the drug core, the quantity of Latanoprost released is compared to the exposed surface area of the drug core with a least square regression line. For the 5.1%, 11.2%, and 17.9% drug cores the slope of the regression lines are 2837.8, 3286.1 and 3411.6, respectively, with $R^2$ coefficients of 0.9925, 0.9701 and 1, respectively. At day 14, the 0.02, 0.07, and 0.32 $mm^2$, cores released about 25 ng, 100 ng and 300 ng of Latanoprost, respectively showing that the quantity of Latanoprost released increases with an increased size of the exposed surface area of the drug core. For the 5.1%, 11.2%, and 17.9% drug cores the slope of the regression lines are 812.19, 1060.1 and 764.35, respectively, with $R^2$ coefficients of 0.9904, 0.9924 and 0.9663, respectively. These values indicate the elution rate of the Latanoprost from the core increases linearly with the surface area of the drug core, consistent with a drug sheath that can control the exposed surface area, as described above. The weak dependence of Latanoprost elution on concentration in the drug core is consistent with droplets of Latanoprost suspended in a drug core matrix and substantial saturation of the drug core matrix with Latanoprost dissolved therein, as described above.

FIG. 7C shows elution data for Latanoprost from 0.32 mm diameter, 0.95 mm long drug cores with concentrations of 5, 10 and 20% and drug weights of 3.5, 7 and 14 µg, respectively, according to embodiments of the present invention. The drug cores were manufactured as described above. The elution rate is plotted in ng per day from 0 to 40 days. The 14 µg core shows rates of approximately 100 ng per day from about 10 to 40 days. The 7 µg core shows comparable rates from 10 to 20 days. These data are consistent with droplets of Latanoprost suspended in a drug core matrix and substantial saturation of the drug core matrix with Latanoprost dissolved therein, as described above.

Table 1 shows the expected parameters for each drug concentration. As shown in FIG. 1C, in vitro results in a buffered saline elution system show that the plug initially elutes approximately 500 ng of Latanoprost per day, dropping off rapidly within 7-14 days to approximately 100 ng/day, depending on the initial concentration of drug.

TABLE 1

| | Drug Elution Properties | | |
|---|---|---|---|
| Total Latanoprost content | 14 μg | 7 μg | 3.5 μg |
| In vitro elution rate | See FIG. 1C | See FIG. 1C | See FIG. 1C |
| Duration | ~100 days | ~45 days | ~25 days |

In many embodiments, the duration of the drug core can be determined based on the calculated time when .about.10% of the original amount of drug remains in drug insert, for example where the elution rate levels out and remains substantially constant at approximately 10 ng/day.

Example 2

Cyclosporin Drug Core Elution Data

Drug cores as described in Example 1 were made with cyclosporin having a concentration of 21.2%. FIG. 8A shows elution profiles of cyclosporin from drug cores into a buffer solution without surfactant and into a buffer solution with surfactant, according to embodiments of the present invention. The buffer solution was made as described above. The solution with surfactant includes 95% buffer and 5% surfactant, UP-1005 Ultra Pure Fluid from Dow Corning, Midland Mich. Work in relation with embodiments of the present invention indicates that in at least some instances, surfactants may be used in in vitro to model in situ elution from the eye as the eye can include natural surfactants, for example Surfactant Protein D, in the tear film. The elution profile of cyclosporin into surfactant is approximately 50 to 100 ng per day from 30 to 60 days. Empirical data from tears of a patient population, for example 10 patients, can be measured and used to refine the in vitro model with appropriate amounts of surfactant. The drug core matrix may be modified in response to the human tear surfactant as determined with the modified in vitro model. The drug core can be modified in many ways in response to the human tear film surfactant, for example with an increased exposed surface area and/or additives to increase an amount of cyclosporine drug dissolved in the core, as described above, to increase elution from the core to therapeutic levels, if appropriate.

Example 3

Bimatoprost Bulk Elution Data

Bulk samples of 1% Bimatoprost having a known diameter of 0.076 cm (0.76 mm) were prepared. The height of each sample was determined from the weight and known diameter of the sample.

TABLE 2

| | Bulk Sample Size | | | |
|---|---|---|---|---|
| Sample | Weight (mg) | Diameter (cm) | Calculated Height (cm) | Exposed Surface Area (cm$^2$) |
| 14-2-10 | 1.9 | 0.076 | 0.42 | 0.109 |
| 14-2-11 | 1.5 | 0.076 | 0.33 | 0.088 |
| 14-2-12 | 1.9 | 0.076 | 0.42 | 0.109 |

Figure 9A:
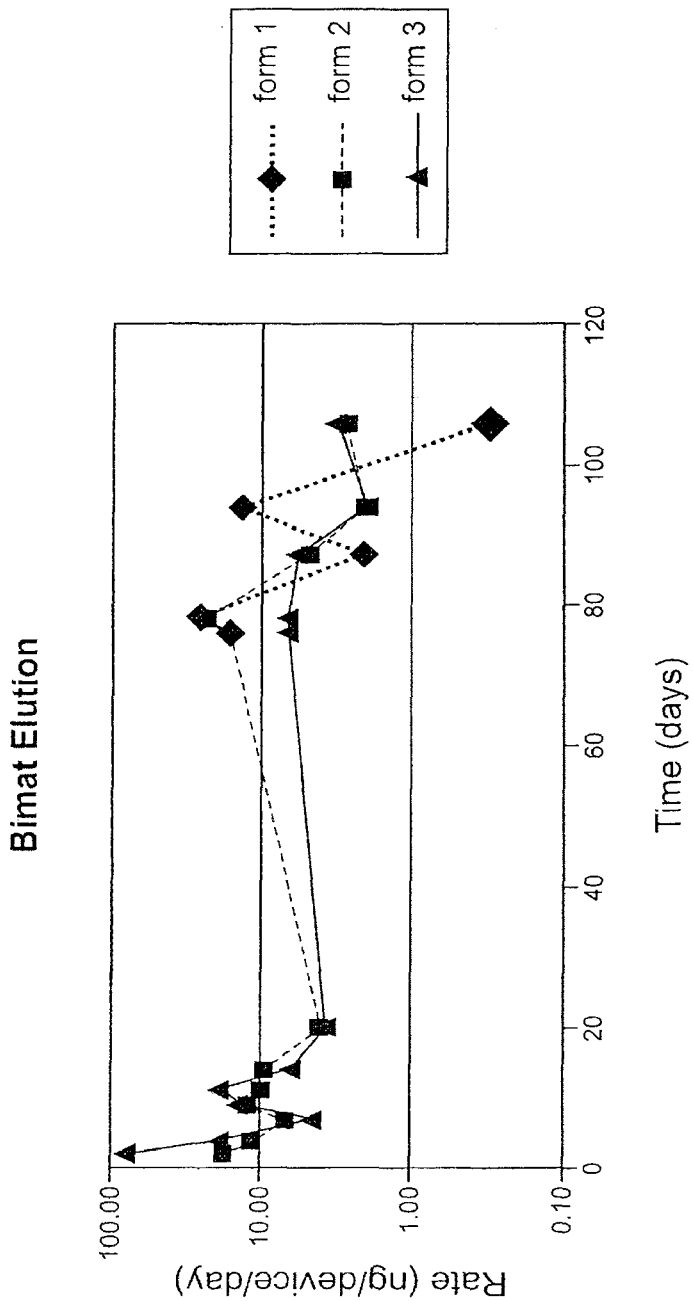
FIG. 9A shows normalized elution profiles in nano-grams per device per day over 100 days for bulk sample of silicone with 1% Bimatoprost, according to embodiments of the present invention.

The calculated heights ranged from 0.33 cm to 0.42 cm. The exposed surface area on each end of each bulk sample was approximately 0.045 cm$^2$, providing volumes of 0.019 cm and 0.015 cm$^3$ for the 0.42 and 0.33 cm samples, respectively. The exposed an exposed surface area of samples calculated from the height and diameter without a drug sheath was approximately 0.1 cm$^2$. Three formulations were evaluated: 1) silicone 4011, 1% Bimatoprost, 0% surfactant; 2) silicone 4011, 1% Bimatoprost, approximately 11% surfactant; and 3) silicone 4011, 1% Bimatoprost, approximately 33% surfactant. The elution data measured for the bulk samples with formulation 1, 2 and 3 were normalized to ng per device per day (ng/device/day) assuming a surface area of the bulk device is 0.1 cm$^2$ and the surface area of the clinical device is 0.00078 cm$^2$ (0.3 mm diameter). FIG. 9A shows normalized elution profiles in ng per device per day over 100 days for bulk sample of silicone with 1% Bimatoprost, assuming an exposed surface diameter of 0.3 mm on the end of the device, according to embodiments of the present invention. The normalized elution profile is about 10 ng per day. The data show approximately zero order release kinetics from about ten days to about 90 days for each of the formulations. These data are consistent with particles of Bimatoprost suspended in a drug core matrix and substantial saturation of the drug core matrix with Bimatoprost dissolved therein, as described above. Similar formulations can be used with drug core sheaths and a shaped exposed surface of the core exposed to the tear to increase the exposed surface area as described above and deliver the drug in therapeutic amounts over an extended period.

In some embodiments, the core can comprise a 0.76 mm diameter core with an exposed surface diameter of 0.76 mm, corresponding to an exposed surface area of 0.0045 cm$^2$. The core can be covered with a sheath to define the exposed surface of the core as described above The normalized elution profile for such a device, based on the bulk sample data above, is approximately 6 times (0.0045 cm$^2$/0.00078 cm$^2$) the elution profile for the device with a 0.3 mm diameter exposed surface area. Thus, a zero order elution profile with an elution rate of about 60 ng per day can be obtained over a period of about 90 days. If the exposed surface area is increased to about 0.0078 cm$^2$, for example with many of the exposed surface shapes as described above, the zero order elution rat is about 100 ng per day over a period of about 90 days. The concentration can also be increased from 1%. Similar elution profiles can be obtained with Latanoprost.

Example 4

Latanoprost Elution Data

Drug cores were manufactured as described above with Latanoprost and silicone 4011, 6385 and/or NaCl. Four formulations were manufactured as follows: A) silicone 4011, approximately 20% Latanoprost, and approximately 20% NaCL; B) silicone 4011, approximately 20% Latanoprost, and approximately 10% NaCl; C) silicone 4011, approximately 10% Latanoprost, and approximately 10% NaCl; and D) silicone 6385, approximately 20% Latanoprost. FIG. 10A shows profiles of elution of Latanoprost form the cores for four formulations of Latanoprost, according to embodiments of the present invention. The results show initial rates of approximately 300 ng per device per day that decreases to about 100 ng per device per day by 3 weeks (21 days). The results shown are for non-sterile drug cores. Similar results have been obtained with sterile drug cores of Latanoprost. These data are consistent with droplets of Latanoprost suspended in a drug core matrix and substantial saturation of the drug core matrix with Latanoprost dissolved therein, as described above.

While the exemplary embodiments have been described in some detail, by way of example and for clarity of understanding, those of skill in the art will recognize that a variety of modification, adaptations, and changes may be employed. For example, multiple delivery mechanisms may be employed, and each device embodiment may be adapted to include features or materials of the other, and further multiple features or multiple materials may be employed in a single device. Hence, the scope of the present invention may be limited solely by the appending claims.

What is claimed is:

1. A punctal plug configured for insertion into a lacrimal canaliculus of a patient, the punctal plug comprising:
    a silicone plug body comprising a drug insert;
    the drug insert comprising:
        a drug core comprising a therapeutic agent contained in a matrix, and
        an impermeable sheath body partially covering the drug core,
    wherein when the punctal plug is inserted into the lacrimal canaliculus of the patient an exposed surface of the drug core is in direct contact with tear fluid to permit diffusion of the therapeutic agent into the tear fluid of the eye.

2. The implant of claim 1, wherein the sheath body is comprised of at least one of polyimide or polyethylene terephthalate.

3. The implant of claim 1, wherein the sheath body includes a distinguishing color that shows placement of one or more of the implant in the lacrimal canaliculus or the insert in the implant.

4. The implant of claim 1, wherein the therapeutic agent comprises one or more of an anti-glaucoma medication, a prostaglandin, a non-steroidal anti-inflammatory drug (NSAID), a lubricant, a surfactant, an inhibitor of angiogenesis, peptides, proteins, or enzymes.

5. The implant of claim 1, wherein the therapeutic agent is selected from the group consisting of latanoprost, bimatoprost, timolol maleate, NSAID, travoprost, and cyclosporin.

6. The implant of claim 5, wherein about 3 micrograms to about 135 micrograms of latanoprost is present in the drug core.

7. The implant of claim 5, wherein about 50 micrograms to about 100 micrograms of latanoprost is present in the drug core.

8. The implant of claim 1, wherein the drug core comprises inclusions of the therapeutic agent in a polymer.

9. The implant of claim 8, wherein the inclusions comprise droplets and the therapeutic agent is latanoprost.

10. The implant of claim 1, wherein the drug insert is further configured to release the therapeutic agent for at least 21 days.

11. The implant of claim 1, wherein the sheath body comprises a polyimide sheath body, and wherein the drug core comprises: silicone and latanoprost.

12. The implant of claim 1, wherein the matrix comprises a non-biodegradable polymer.

13. The implant of claim 12, wherein the non-biodegradable polymer is selected from the group consisting of silicone, an acrylate, a polyethylene, polyurethane, and polyester.

14. The implant of claim 1, wherein the concentration of therapeutic agent in the drug core is at least 20% by weight of the drug core.

15. The implant of claim 1, wherein the drug core comprises a non-homogenous mixture of silicone and the therapeutic agent.

16. The implant of claim 1, wherein the drug insert has a diameter of about 0.006 inches to about 0.025 inches.

17. A method for the treatment of glaucoma in an eye, the method comprising: placing a punctal plug in a lacrimal canaliculus of the eye, wherein the punctal plug comprises;
    a silicone plug body comprising a drug insert;
    the drug insert comprising:
    a drug core comprising a therapeutic agent contained in a matrix; and
    an impermeable sheath body, wherein the drug core is positioned within the sheath body, wherein the sheath body is configured to provide aproximal exposed proximal end of the drug insert in direct contact with tear fluid that releases therapeutic agent to the eye when the drug insert is disposed within the punctal plug and the punctal plug is inserted into the lacrimal canaliculus of a patient.

* * * * *